US010150750B2

(12) United States Patent
Vautravers et al.

(10) Patent No.: US 10,150,750 B2
(45) Date of Patent: Dec. 11, 2018

(54) PROCESS FOR THE OXIDATION OF ORGANIC CARBONYL COMPOUNDS

(71) Applicant: BASF SE, Ludwigshafen (DE)

(72) Inventors: Nicolas Vautravers, Mannheim (DE); Joaquim H. Teles, Waldsee (DE); Andrei-Nicolae Parvulescu, Ruppertsberg (DE); Ulrich Müller, Neustadt (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/034,249

(22) PCT Filed: Nov. 5, 2014

(86) PCT No.: PCT/EP2014/073812
§ 371 (c)(1),
(2) Date: May 4, 2016

(87) PCT Pub. No.: WO2015/067657
PCT Pub. Date: May 14, 2015

(65) Prior Publication Data
US 2016/0264543 A1 Sep. 15, 2016

(30) Foreign Application Priority Data
Nov. 5, 2013 (EP) .................................... 13191690

(51) Int. Cl.
| *B01J 29/06* | (2006.01) |
| *B01J 21/16* | (2006.01) |
| *C07C 49/00* | (2006.01) |
| *C07D 313/04* | (2006.01) |
| *B01J 27/18* | (2006.01) |
| *B01J 29/70* | (2006.01) |
| *B01J 31/02* | (2006.01) |
| *C07B 41/12* | (2006.01) |

(52) U.S. Cl.
CPC ........ *C07D 313/04* (2013.01); *B01J 27/1806* (2013.01); *B01J 29/7088* (2013.01); *B01J 31/0209* (2013.01); *C07B 41/12* (2013.01)

(58) Field of Classification Search
CPC .... C07D 313/04; C07B 41/12; B01J 31/0209; B01J 27/1806; B01J 29/7088; B01J 21/16; B01J 29/06; C07C 49/00
USPC .................... 549/272; 502/63, 84; 568/303
See application file for complete search history.

(56) References Cited

U.S. PATENT DOCUMENTS

| 5,736,478 | A | 4/1998 | Cortright et al. |
| 5,968,473 | A | 10/1999 | Valencia et al. |
| 6,132,595 | A * | 10/2000 | Bogdan ................. B01J 29/068 208/138 |
| 6,306,364 | B1 | 10/2001 | Valencia et al. |
| 6,344,583 | B1 | 2/2002 | Canos et al. |
| 7,326,401 | B2 | 2/2008 | Tatsumi et al. |
| 7,432,406 | B1 * | 10/2008 | Chen ..................... B01J 29/605 585/654 |
| 7,439,409 | B1 * | 10/2008 | Jan ............................ C07C 5/31 585/251 |
| 2005/0158238 | A1 * | 7/2005 | Tatsumi ............... C01B 37/005 423/702 |

FOREIGN PATENT DOCUMENTS

| CN | 1185224 C | 1/2005 |
| CN | 100522808 C | 8/2009 |
| EP | 2487173 A1 | 8/2012 |
| WO | WO-0181291 A2 | 11/2001 |
| WO | WO-03/074422 A1 | 9/2003 |

OTHER PUBLICATIONS

International Search Report with Written Opinion of International Searching Authority for PCT/EP2014/073812 dated Jan. 14, 2015.
Camblor, M., "Synthesis and Structural Characterization of MWW Type Zeolite ITQ-1, the Pure Silica Analog of MCM-22 and SSZ-25", J. Phys. Chem. B. 1998, vol. 102. pp. 44-51.
Corma, A., et al., "A new, alternative, halogen-free synthesis for the fragrance compound Melonal using zeolites and mesoporous as oxidation catalysts", Journal of Catalysis, 2005, vol. 234, pp. 96-100.
Corma, A., et al., "Sn-zeolite beta as a heterogenenous chemoselective catalyst for Baeyer-Villiger oxidations", Nature, 2001, vol. 412, pp. 423-425.
Liu, G., et al., "Hydrothermal sythesis of MWW-type stannosilicate and its post-structural transformation to MCM-56 analogue", Microporous and Mesoporous Materials, 2013, vol. 165, pp. 210-218.
Chinese Office Action with English Translation for Chinese Application No. 201480072233, dated May 28, 2018.

* cited by examiner

*Primary Examiner* — Taylor V Oh
(74) *Attorney, Agent, or Firm* — Drinker Biddle & Reath LLP

(57) ABSTRACT

A process for the oxidation of an organic carbonyl compound comprising reacting the compound, optionally in the presence of a solvent, with hydrogen peroxide in the presence of a catalyst comprising a tin-containing zeolitic material and at least one potassium salt.

13 Claims, No Drawings

PROCESS FOR THE OXIDATION OF ORGANIC CARBONYL COMPOUNDS

CROSS-REFERENCE TO RELATED APPLICATIONS

This application is a national stage application (under 35 U.S.C. § 371) of PCT/EP2014/073812, filed Nov. 5, 2014, which claims benefit of European Application No. 13191690.0, filed Nov. 5, 2013, both applications of which are incorporated herein by reference in their entirety.

The present invention relates to a process for the oxidation of an organic carbonyl compound, in particular a Baeyer-Villiger-type oxidation of an organic carbonyl compound, in the presence of a catalyst comprising a tin-containing zeolitic material having an MWW-type framework structure which zeolitic material has a low boron content.

BACKGROUND OF THE INVENTION

Oxidation reactions of organic compounds and in particular the Bayer-Villiger reaction is of considerable interest in order to convert readily available carbonyl compounds in more complex and valuable products.

The use of peroxyacetic acid in the Baeyer-Villiger oxidation as described in Justus Liebigs Ann. Chem. 681 (1965), pages 28-30 is a common method for the oxidation of ketones to the respective lactones. However, the use of peroxyacetic acid involves considerable disadvantages regarding cost-effectiveness and safety aspects, in particular in industrial-scale processes.

In Nature 412 (2001), pages 423-425, and in Journal of Catalysis 234 (2005), pages 96-100, a tin-containing zeolite Beta is described for the use in the Baeyer-Villiger reaction. Further, in Journal of Catalysis 234 (2005), pages 96-100, a Baeyer-Villiger reaction is disclosed wherein citral is used as starting material. The experiments carried out regarding this reaction show that by use of the tin-containing zeolite Beta a selectivity to melonal of at most 20% is achieved. Generally, tin-containing zeolite Beta materials are comparatively difficult to prepare which renders this prior art process disadvantageous since the synthesis of the catalyst, disclosed in U.S. Pat. No. 5,968,473 and U.S. Pat. No. 6,306,364, it is technically difficult to scale-up due to low yield, high synthesis times more than 15 days, the use of HF and chlorinated Sn precursor compounds.

Furthermore, in Microporous and Mesoporous Materials 165 (2013), pages 210-218, the use of a tin-containing zeolitic material having an MWW framework structure in the Baeyer-Villiger reaction of 2-adamantanone is described. According to this document, the zeolitic materials are obtained from a boron-containing precursor material which is not subjected to deboronation resulting in a material having a comparatively high boron content.

WO 03/074422 A1 and U.S. Pat. No. 7,326,401 B2 describe a process for synthesizing a zeolite material having MWW structure. A tin containing MWW is mentioned in the description, having a very high tin loading of about 4.7 weight-%. This tin containing MWW is prepared from a B-MWW zeolite precursor which is deboronated by acid treatment before the Sn is introduced.

DETAILED DESCRIPTION OF THE INVENTION

It was an object of the present invention to provide a process for the Baeyer-Villiger oxidation of an organic carbonyl compound, which exhibits a high selectivity to the oxidation product, based on both the organic carbonyl compound to be oxidized and the oxidation agent hydrogen peroxide.

Surprisingly, it was found that this object can be achieved if the Baeyer-Villiger oxidation reaction is carried out in the presence of a tin-containing zeolitic material and in the presence of a potassium additive.

Therefore, the present invention relates to a process for the oxidation of an organic carbonyl compound of formula (I)

wherein $R_1$ and $R_2$ are independently from one another a linear or branched alkyl residue, a linear or branched alkenyl residue, an aryl or heteroaryl residue, or a hydrogen atom with the proviso that $R_1$ and $R_2$ are not simultaneously a hydrogen atom, said process comprising (i) providing a liquid mixture comprising the compound of formula (I), hydrogen peroxide, at least one at least partially dissolved potassium salt, and optionally a solvent;

(ii) reacting the compound of formula (I) with the hydrogen peroxide in the liquid mixture in the presence of a catalyst comprising a tin-containing zeolitic material, obtaining a compound of formula (II)

wherein, if neither $R_1$ nor $R_2$ is a hydrogen atom, $R_1$ and $R_2$ may form, together with the carbonyl group or the carboxyl group, a ring and the compound of formula (I) is

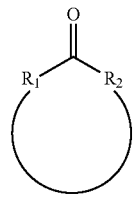

and the compound of formula (II) is

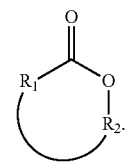

Surprisingly, it was further found that the object of the present can be achieved irrespective which framework structure the tin-containing zeolitic material has, irrespective which tin content the tin-containing zeolitic material has, irrespective whether the reaction is carried out in batch mode using the zeolitic material as such or in continuous mode using the zeolitic material comprised in a molding, and irrespective which potassium salt is used as additive.

Step (i)

The Compound of Formula (I)

Regarding the organic carbonyl compound of formula (I)

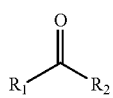

there are generally no specific restrictions as far as the chemical nature of the residues $R_1$ and $R_2$ is concerned provided that the compound of formula (I) can be oxidized to obtain the compound of formula (II).

Preferably, $R_1$ and $R_2$ are independently from one another a linear or branched alkyl residue having from 1 to 20 carbon atoms, a linear or branched alkenyl residue having from 2 to 20 carbon atoms, an aryl or heteroaryl residue having from 4 to 20 carbon atoms, or a hydrogen atom. Preferably, if neither $R_1$ nor $R_2$ is a hydrogen atom, $R_1$ and $R_2$ may form together with the carbonyl group in the compound of formula (I) or the carboxyl group in the compound of formula (II) a ring having from 4 to 20 carbon atoms. Therefore, the present invention relates to the process above, wherein $R_1$ and $R_2$ are independently from one another a linear or branched alkyl residue having from 1 to 20 carbon atoms, a linear or branched alkenyl residue having from 2 to 20 carbon atoms, an aryl or heteroaryl residue having from 4 to 20 carbon atoms, or a hydrogen atom and wherein, if neither $R_1$ nor $R_2$ is a hydrogen atom, $R_1$ and $R_2$ may form, together with the carbonyl group or the carboxyl group, a ring having from 4 to 20 carbon atoms.

The linear or branched alkyl residue having from 1 to 20 carbon atoms may be suitably substituted, for example with either at least one halogen atom such F, Cl, Br, I, and/or with at least one alkenyl group preferably having from 2 to 8 carbon atoms, and/or with at least one aryl group or heteroaryl group preferably having from 4 to 10 carbon atoms wherein the at least one heteroatom comprised in the heteroaryl group is preferably S, O, or N, and/or with at least one aralkyl group having from 4 to 10 carbon atoms, and/or with at least one heteroaralkyl group having from 4 to 10 carbon atoms wherein the at least one heteroatom comprised in the heteroaralkyl group is preferably S, O, or N. The term "aralkyl group" as used in this context of the present invention relates to an aryl group which is bound to the linear or branched alkyl residue having from 1 to 20 carbon atoms and which is substituted with at least one alkyl group. The term "heteroaralkyl group" as used in this context of the present invention relates to a heteroaryl group which is bound to the linear or branched alkyl residue having from 1 to 20 carbon atoms, either via carbon atom or a suitable heteroatom of the heteroaryl group, and which is substituted with at least one alkyl group. Further, the linear or branched alkyl residue having from 1 to 20 carbon atoms may comprise at least one heteroatom, preferably N, O, or S, in the carbon atom chain.

Preferably, the linear or branched alkyl residue has from 1 to 18, more preferably from 1 to 14, more preferably from 1 to 12, more preferably from 1 to 11, more preferably from 1 to 10, more preferably from 1 to 9 carbon atoms, more preferably from 1 to 8 carbon atoms such as 1, 2, 3, 4, 5, 6, 7, or 8 carbon atoms.

The linear or branched alkenyl residue having from 2 to 20 carbon atoms may be suitably substituted, for example with either at least one halogen atom such F, Cl, Br, I, and/or with at least one alkyl group preferably having from 2 to 8 carbon atoms, and/or with at least one aryl group or heteroaryl group preferably having from 4 to 10 carbon atoms wherein the at least one heteroatom comprised in the heteroaryl group is preferably S, O, or N, and/or with at least one aralkyl group having from 4 to 10 carbon atoms, and/or with at least one heteroaralkyl group having from 4 to 10 carbon atoms wherein the at least one heteroatom comprised in the heteroaralkyl group is preferably S, O, or N. The term "aralkyl group" as used in this context of the present invention relates to an aryl group which is bound to the linear or branched alkenyl residue having from 2 to 20 carbon atoms and which is substituted with at least one alkyl group. The term "heteroaralkyl group" as used in this context of the present invention relates to a heteroaryl group which is bound to the linear or branched alkenyl residue having from 2 to 20 carbon atoms, either via carbon atom or a suitable heteroatom of the heteroaryl group, and which is substituted with at least one alkyl group. Further, the linear or branched alkenyl residue having from 2 to 20 carbon atoms may comprise at least one heteroatom, preferably N, O, or S, in the carbon atom chain.

Preferably, the linear or branched alkenyl residue has from 2 to 18, more preferably from 2 to 14, more preferably from 2 to 12, more preferably from 2 to 11, more preferably from 2 to 10, more preferably from 2 to 9 carbon atoms, more preferably from 2 to 8 carbon atoms such as 2, 3, 4, 5, 6, 7, or 8 carbon atoms.

The aryl or heteroaryl residue having from 4 to 20 carbon atoms may be suitably substituted, for example with either at least one halogen atom such F, Cl, Br, I, and/or with at least one alkyl group preferably having from 2 to 8 carbon atoms, and/or with at least one aryl group or heteroaryl group preferably having from 4 to 10 carbon atoms wherein the at least one heteroatom comprised in the heteroaryl group is preferably S, O, or N, and/or with at least one aralkyl group having from 4 to 10 carbon atoms, and/or with at least one heteroaralkyl group having from 4 to 10 carbon atoms wherein the at least one heteroatom comprised in the heteroaralkyl group is preferably S, O, or N. The term "aralkyl group" as used in this context of the present invention relates to an aryl group which is bound to the aryl or heteroaryl residue having from 4 to 20 carbon atoms and which is substituted with at least one alkyl group. The term "heteroaralkyl group" as used in this context of the present invention relates to a heteroaryl group which is bound to the aryl or heteroaryl residue having from 4 to 20 carbon atoms, either via carbon atom or a suitable heteroatom of the heteroaryl group, and which is substituted with at least one alkyl group. Further, the heteroaryl residue having from 4 to 20 carbon atoms may comprise, as at least one heteroatom, preferably N, O, or S.

Preferably, the aryl or heteroaryl residue has from 4 to 18, more preferably from 4 to 14, more preferably from 4 to 12, more preferably from 4 to 11, more preferably from 4 to 10, more preferably from 4 to 9 carbon atoms, more preferably from 4 to 8 carbon atoms such as 4, 5, 6, 7, or 8 carbon atoms.

As mentioned above, $R_1$ and $R_2$ are independently from one another a linear or branched alkyl residue, a linear or branched alkenyl residue, an aryl or heteroaryl residue, or a hydrogen atom, with the proviso that $R_1$ and $R_2$ are not simultaneously a hydrogen atom.

Therefore, the compound of formula (I) may comprise a residue $R_1$ which is a linear or branched alkyl residue and a residue $R_2$ which is hydrogen. Further, the compound of formula (I) may comprise a residue $R_1$ which is a linear or branched alkenyl residue and a residue $R_2$ which is hydrogen. Further, the compound of formula (I) may comprise a residue $R_1$ which is an aryl or heteroaryl residue and a residue $R_2$ which is hydrogen. Further, the compound of formula (I) may comprise a residue $R_2$ which is a linear or branched alkyl residue and a residue $R_1$ which is hydrogen. Further, the compound of formula (I) may comprise a residue $R_2$ which is a linear or branched alkenyl residue and a residue $R_1$ which is hydrogen. Further, the compound of formula (I) may comprise a residue $R_2$ which is an aryl or heteroaryl residue and a residue $R_1$ which is hydrogen. Further, the compound of formula (I) may comprise a residue $R_1$ which is a linear or branched alkyl residue and a residue $R_2$ which is a linear or branched alkyl residue. Further, the compound of formula (I) may comprise a residue $R_1$ which is a linear or branched alkenyl residue and a residue $R_2$ which is a linear or branched alkenyl residue. Further, the compound of formula (I) may comprise a residue $R_1$ which is an aryl or heteroaryl residue and a residue $R_2$ which is an aryl or heteroaryl residue. Further, the compound of formula (I) may comprise a residue $R_1$ which is a linear or branched alkyl residue and a residue $R_2$ which is a linear or branched alkenyl residue. Further, the compound of formula (I) may comprise a residue $R_1$ which is a linear or branched alkyl residue and a residue $R_2$ which is an aryl or heteroaryl residue. Further, the compound of formula (I) may comprise a residue $R_1$ which is a linear or branched alkenyl residue and a residue $R_2$ which is an aryl or heteroaryl residue. Further, the compound of formula (I) may comprise a residue $R_2$ which is a linear or branched alkyl residue and a residue $R_1$ which is a linear or branched alkenyl residue. Further, the compound of formula (I) may comprise a residue $R_2$ which is a linear or branched alkyl residue and a residue $R_1$ which is an aryl or heteroaryl residue. Further, the compound of formula (I) may comprise a residue $R_2$ which is a linear or branched alkenyl residue and a residue $R_1$ which is an aryl or heteroaryl residue. Further, it is conceivable that the compound of formula (I) may be a mixture of two or more of these compounds.

Further, if neither $R_1$ nor $R_2$ is a hydrogen atom, $R_1$ and $R_2$ may form, together with the carbonyl group in the compound of formula (I) or the carboxyl group in the compound of formula (II), a ring, preferably having from 4 to 20 carbon atoms. The term "a ring having from 4 to 20 carbon atoms" as used in the context of the present invention relates to a ring with a carbon atom chain length of from 4 to 20 carbon atoms.

Preferably, the ring has from 4 to 18, more preferably from 5 to 16, such as 5, 6, 7, 8, 9, 10, 11, 12, 13, 14, 15, or 16 carbon atoms, preferably 5, 6, 8, 12, 15 or 16 carbon atoms. Preferred compounds of formula (I) wherein neither $R_1$ nor $R_2$ is a hydrogen atom and wherein $R_1$ and $R_2$ form, together with the carbonyl group in the compound of formula (I) or the carboxyl group in the compound of formula (II), a ring, include cyclopentanone, cyclohexanone, cycloheptanone, cyclooctanone, cyclododecanone, cyclopentadecanone, cyclohexadecanone, 2-pentylcyclopentanone, 2-heptylcyclopentanone, and cyclohexadec-8-en-1-one.

Therefore, the present invention relates to a process for the oxidation of a cyclic ketone of formula (I)

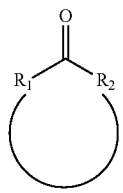

wherein the ring formed by $R_1$, $R_2$, and the carbonyl carbon atom has from 4 to 20, preferably from 4 to 18, more preferably from 5 to 16 carbon, atoms preferably 5, 6, 8, 12, 15 or 16 carbon atoms, said process comprising (i) providing a liquid mixture comprising the compound of formula (I), hydrogen peroxide, at least one at least partially dissolved potassium salt, and optionally a solvent;

(ii) reacting the compound of formula (I) with hydrogen peroxide in the liquid mixture in the presence of a catalyst comprising a tin-containing zeolitic material, obtaining a compound of formula (II)

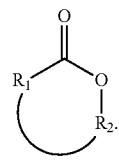

Further, the present invention relates to said process, wherein the cyclic ketone of formula (I) is selected from the group consisting of cyclopentanone, cyclohexanone, cycloheptanone, cyclooctanone, cyclododecanone, cyclopentadecanone, cyclohexadecanone, 2-pentylcyclopentanone, 2-heptylcyclopentanone, cyclohexadec-8-en-1-one, and a mixture of two or more thereof, the cyclic ketone of formula (I) preferably being cyclohexanone.

The ring of the cyclic ketone of formula (I) may be suitably substituted, for example with either at least one halogen atom such F, Cl, Br, I, and/or with at least one alkyl group preferably having from 2 to 8 carbon atoms, and/or with at least one aryl group or heteroaryl group preferably having from 4 to 10 carbon atoms wherein the at least one heteroatom comprised in the heteroaryl group is preferably S, O, or N, and/or with at least one aralkyl group having from 4 to 10 carbon atoms, and/or with at least one heteroaralkyl group having from 4 to 10 carbon atoms wherein the at least one heteroatom comprised in the heteroaralkyl group is preferably S, O, or N. The term "aralkyl group" as used in this context of the present invention relates to an aryl group which is bound to the ring and which is substituted with at least one alkyl group. The term "heteroaralkyl group" as used in this context of the present invention relates to a heteroaryl group which is bound to the ring, either via carbon atom or a suitable heteroatom of the heteroaryl group, and which is substituted with at least one alkyl group. Further, the ring may comprise at least one heteroatom, preferably N, O, or S, in the carbon atom chain. Further, the chain of carbon atoms forming the ring together with the carbonyl or carboxyl group according to formula (I) may comprise at least one C—C double bond. Further, it is conceivable that the compound of formula (I) may be a mixture at least compound having a ring formed together with the carbonyl group or the carboxyl group according to formula (I) and at least one compound not having such a ring.

According to the present invention, the compound of formula (I) may contain at least one C—C double bond. This at least one C—C double bond may be located anywhere in the residues $R_1$ and/or $R_2$ or in the ring formed together with the carbonyl group or the carboxyl group according to formula (I). For example, depending on the size of $R_1$ and/or $R_2$ or in the ring formed by $R_1$, $R_2$ together with the carbonyl group in the compound of formula (I), the compound of formula (I) may comprise 1, 2, 3 or more C—C double bonds. Therefore, the present invention also relates to the process above, wherein the compound of formula (I) contains at least one C—C double bond.

According to the present invention, the compound of formula (I) may contain a C—C double bond in alpha position to the carbonyl group according to formula (I). Thus, according to the present invention, the compound of formula (I) can be an alpha,beta unsaturated compound. In addition to the C—C double bond in alpha position to the carbonyl group according to formula (I), the compound of formula (I) may comprise 1, 2 or more additional C—C double bonds. Therefore, the present invention also relates to the process above, wherein the compound of formula (I) contains a C—C double bond in alpha position to the carbonyl group.

Further according to the present invention, the compound of formula (I) may contain a C—C double bond in alpha position to the carbonyl group according to formula (I) wherein the residue $R_2$ is a hydrogen atom. Therefore, the present invention also relates to the process above, wherein $R_1$ contains a C—C double bond in alpha position to the carbonyl group and $R_2$ is a hydrogen atom.

The Solvent

Depending on the chemical nature of the organic carbonyl compound, it may be conceivable that the organic carbonyl compound is liquid under the reaction conditions opplied in (ii). In this case, it may be conceivable to carry out the reaction without adding a solvent, and to provide in (i) a liquid mixture which does not contain a solvent. Preferably, at least one solvent is used for the reaction according to (ii), and in (i), a liquid mixture is provided containing a solvent. Therefore, the present invention relates to the process as described above, comprising
(i) providing a liquid mixture comprising the compound of formula (I), hydrogen peroxide, at least one at least partially dissolved potassium salt, and a solvent.

Generally, the solvent can be chosen according to the chemical nature of the organic carbonyl compound. Preferably, the solvent is a polar solvent, more preferably a polar aprotic solvent. Therefore, the present invention relates to the process as described above, comprising
(i) providing a liquid mixture comprising the compound of formula (I), hydrogen peroxide, at least one at least partially dissolved potassium salt, and a polar solvent, preferably a polar aprotic solvent.

More preferably, the solvent is selected from the group consisting of acetonitrile, 1,2-dichloroethane, dichloromethane, chloroform, propionitrile, 1,4-dioxane, methyl tert-butyl ether, diethyl ether, dibutyl ether, ethyl acetate, butyl acetate, dimethyl carbonate, ethylene carbonate, propylene carbonate, and mixtures of two or more thereof. More preferably, the solvent is 1,2-dichloroethane, 1,4-dioxane, acetonitrile, or a mixture thereof. Therefore, the present invention also relates to the process as described above, comprising
(i) providing a liquid mixture comprising the compound of formula (I), hydrogen peroxide, at least one at least partially dissolved potassium salt, and a polar solvent selected from the group consisting of acetonitrile, 1,2-dichloroethane, dichloromethane, chloroform, propionitrile, 1,4-dioxane, methyl tert-butyl ether, diethyl ether, dibutyl ether, ethyl acetate, butyl acetate, dimethyl carbonate, ethylene carbonate, propylene carbonate, and mixtures of two or more thereof, the solvent more preferably being 1,2-dichloroethane, 1,4-dioxane, acetonitrile, or a mixture of two or three thereof.

The Hydrogen Peroxide

The hydrogen peroxide employed in (i) can be prepared according to every conceivable method. It is conceivable to obtain the hydrogen peroxide by converting sulphuric acid into peroxodisulphuric acid by anodic oxidation with simultaneous evolution of hydrogen at the cathode. Hydrolysis of the peroxodisulphuric acid then leads via peroxomonosulphuric acid to hydrogen peroxide and sulphuric acid which is thus obtained back. The preparation of hydrogen peroxide from the elements is also conceivable. Depending on the specific preparation method, the hydrogen peroxide can be, for example, employed in the form of an aqueous or an aqueous/methanolic hydrogen peroxide solution, preferably in the form of an aqueous hydrogen peroxide solution. In case an aqueous hydrogen peroxide solution is employed, the content of the solution with respect to hydrogen peroxide is preferably in the range of from 20 to 90 weight-%, preferably from 30 to 85 weight-%, more preferably from 40 to 75 weight-%.

According to the present invention, it is preferred to employ a solution comprising hydrogen peroxide which is obtained as crude hydrogen peroxide solution by extraction of a mixture which results from a process known as anthraquinone process by means of which virtually the entire world production of hydrogen peroxide is produced (see, e.g., Ullmann's Encyclopedia of Industrial Chemistry, 5th edition, volume A 13 (1989) pages 443-466) wherein a solution of an anthraquinone is used containing an alkyl group preferably having of from 2 to 10 carbon atoms, more preferably at least 5 carbon atoms such as 5 carbon atoms or 6 carbon atoms and where the solvent used usually consists of a mixture of two different solvents. This solution of the anthraquinone is usually referred to as the working solution. In this process, the hydrogen peroxide formed in the course of the anthraquinone process is generally separated by extraction from the respective working solution after a hydrogenation/re-oxidation cycle. Said extraction can be performed preferably with essentially pure water, and the crude aqueous hydrogen peroxide solution is obtained. While it is generally possible to further purify the thus obtained crude aqueous hydrogen peroxide solution by distillation, it is preferred, according to the present invention, to use such crude aqueous hydrogen peroxide solution which has not been subjected to purification by distillation. Further, it is generally possible to subject the crude aqueous hydrogen peroxide solution to a further extraction stage wherein a suitable extracting agent, preferably an organic solvent is used. More preferably, the organic solvent used for this further extraction stage is the same solvent which is used in the anthraquinone process. Preferably the extraction is performed using just one of the solvents in the working solution and most preferably using just the most nonpolar solvent of the working solution. In case the crude aqueous hydrogen peroxide solution is subjected to such further extraction stage, a so-called crude washed hydrogen peroxide solution is obtained. Preferably, the crude washed hydrogen peroxide solution is used as hydrogen peroxide solution.

In order to provide a sufficient stability of the hydrogen peroxide during extraction with water, preferably essentially pure water, suitable stabilizing agents are usually added to the water, preferably the essentially pure water used. In particular, strong inorganic acids and/or chelating agents are to be mentioned. According to preferred extraction processes, small amounts of nitrates and/or phosphates and pyrophosphates, respectively, are added as stabilizing agents, either as acids or as sodium salts. These stabilizing agents are usually added in amounts so that the crude aqueous hydrogen peroxide solution contains from 50 to 400 weight-ppm sodium cations, from 100 to 700 weight-ppm phosphorus calculated as phosphate ($PO_4^{3-}$), and from 50 to 400 weight-ppm nitrate anions, in each case calculated with respect to hydrogen peroxide contained in the crude aqueous hydrogen peroxide solution. Preferred ranges are, for example, from 50 to 200 weight-ppm or from 50 to 100 weight-ppm of sodium cations, from 100 to 500 weight-ppm or from 100 to 300 weight-ppm of phosphorus, and 50 to 200 weight-ppm or 50 to 100 weight-ppm of nitrate. Further, it is conceivable that other stabilizing agents such as stannites like sodium stannite ($Na_2SnO_2$) and/or organic phosphonic acids, in particular organic diphosphonic acids like etidronic acid are used. Preferably, the aqueous hydrogen peroxide stream comprises sodium with a molar ratio of sodium relative to hydrogen peroxide in the range of from $1 \times 10^{-6}:1$ to $250 \times 10^{-6}:1$, more preferably from $5 \times 10^{-6}:1$ to $50 \times 10^{-6}:1$. More preferably, the preferably employed aqueous hydrogen peroxide solution employed in (i) is the only source via which sodium is introduced in the liquid mixture provided in (i).

Therefore, the present invention also relates to the process as described above, wherein the liquid mixture provided in (i) contains sodium in a molar ratio of sodium relative to hydrogen peroxide in the range of from $1 \times 10^{-6}:1$ to $250 \times 10^{-6}:1$, preferably from $5 \times 10^{-6}:1$ to $50 \times 10^{-6}:1$. Therefore, the present invention also relates to the process as defined above, wherein the hydrogen peroxide is employed in (i) in the form of an aqueous hydrogen peroxide solution having a hydrogen peroxide concentration in the range of from 20 to 90 weight-%, preferably from 30 to 85 weight-%, more preferably from 40 to 75 weight-%, based on the total weight of the aqueous hydrogen peroxide solution, wherein the aqueous hydrogen peroxide solution further comprises sodium at a molar ratio of sodium relative to hydrogen peroxide in the range of from $1 \times 10^{-6}:1$ to $250 \times 10^{-6}:1$, preferably from $5 \times 10^{-6}:1$ to $50 \times 10^{-6}:1$.

Thus, the present invention also relates to the process as described above, comprising
(i) providing a liquid mixture comprising the compound of formula (I), hydrogen peroxide, at least one at least partially dissolved potassium salt, and a polar solvent selected from the group consisting of acetonitrile, 1,2-dichloroethane, dichloromethane, chloroform, propionitrile, 1,4-dioxane, methyl tertbutyl ether, diethyl ether, dibutyl ether, ethyl acetate, butyl acetate, dimethyl carbonate, ethylene carbonate, propylene carbonate, and mixtures of two or more thereof, the solvent more preferably being 1,2-dichloroethane, 1,4-dioxane, acetonitrile, or a mixture of two or three thereof,
wherein for providing the liquid mixture in (i), the hydrogen peroxide is employed in (i) in the form of an aqueous hydrogen peroxide solution having a hydrogen peroxide concentration in the range of from 20 to 90 weight-%, preferably from 30 to 85 weight-%, more preferably from 40 to 75 weight-%, based on the total weight of the aqueous hydrogen peroxide solution, wherein the aqueous hydrogen peroxide solution further comprises sodium at a molar ratio of sodium relative to hydrogen peroxide in the range of from $1 \times 10^{-6}:1$ to $250 \times 10^{-6}:1$, preferably from $5 \times 10^{-6}:1$ to $50 \times 10^{-6}:1$.

The Potassium Salt

According to (i), the liquid mixture comprises in addition to the compound of formula (I) at least one at least partially dissolved potassium salt.

Regarding the chemical nature of the at least one potassium salt, no specific restrictions exist provided that the potassium salt can be at least partially dissolved in the liquid mixture provided in (i). Preferably, the at least one potassium salt is selected from the group consisting of at least one inorganic potassium salt, at least one organic potassium salt, and combinations of at least one inorganic potassium salt and at least one organic potassium salt.

Preferably, the at least one potassium salt is selected from the group consisting of at least one inorganic potassium salt selected from the group consisting of potassium hydroxide, potassium halides, potassium nitrate, potassium sulfate, potassium hydrogen sulfate, potassium hydrogen phosphate, potassium dihydrogen phosphate, potassium perchlorate, at least one organic potassium salt selected from the group consisting of potassium carbonate, potassium hydrogen carbonate, potassium salts of aliphatic saturated carboxylic acids such as monocarboxylic acids preferably having from 1 to 6, more preferably from 1 to 5, more preferably from 1 to 4, more preferably from 1 to 3 carbon atoms such as formic acid, acetic acid, propionic acid, dicarboxylic acids preferably having from 2 to 6, more preferably from 2 to 4 carbon atoms such as oxalic acid, malonic acid, succinic acid, tartaric acid, tricarboxylic acids preferably having from 4 to 10 carbon atoms such as citric acid or isocitric acid or propane-1,2,3-tricarboxylic acid, tetracarboxylic acids, and a combination of at least one of the at least one inorganic potassium salts and at least one of the at least one organic potassium salts.

More preferably, the organic potassium salt is selected from the group consisting of potassium salts of aliphatic saturated monocarboxylic acids preferably having 1, 2, 3, 4, 5 or 6 carbon atoms, potassium carbonate, and potassium hydrogen carbonate. More preferably, the organic potassium salt is selected from the group consisting of potassium formate, potassium acetate, potassium propionate, potassium carbonate, and potassium hydrogen carbonate. More preferably, the organic potassium salt is selected from the group consisting of potassium formate, potassium acetate, potassium carbonate, and potassium hydrogen carbonate. More preferably, the organic potassium salt is selected from the group consisting of potassium formate and potassium acetate.

More preferably, the at least one potassium salt is selected from the group consisting of potassium nitrate, potassium dihydrogen phosphate, potassium formate, and a combination of two or more thereof.

Thus, the present invention also relates to the process as described above, comprising
(i) providing a liquid mixture comprising the compound of formula (I), hydrogen peroxide, at least one at least partially dissolved potassium salt, and a polar solvent selected from the group consisting of acetonitrile, 1,2-dichloroethane, dichloromethane, chloroform, propionitrile, 1,4-dioxane, methyl tert-butyl ether, diethyl ether, dibutyl ether, ethyl acetate, butyl acetate, dimethyl carbonate, ethylene carbonate, propylene carbonate, and mixtures of two or more thereof, the solvent more preferably being 1,2-dichloroethane, 1,4-dioxane, acetonitrile, or a mixture of two or three thereof, wherein for providing the liquid mixture in (i), the hydrogen peroxide is employed in (i) in the form of an aqueous hydrogen peroxide solution having a hydrogen peroxide concentration in the range of from 30 to 80 weight-%, more preferably from 35 to 75 weight-%, more preferably from 40 to 70 weight-%, based on the total weight of the aqueous hydrogen peroxide solution, wherein the aqueous hydrogen peroxide solution further comprises sodium at a molar ratio of sodium relative to hydrogen peroxide in the range of from $1\times10^{-6}:1$ to $250\times10^{-6}:1$, preferably from $5\times10^{-6}:1$ to $50\times10^{-6}:1$, and wherein the at least one potassium salt is selected from the group consisting of at least one inorganic potassium salt selected from the group consisting of potassium hydroxide, potassium halides, potassium nitrate, potassium sulfate, potassium hydrogen sulfate, potassium hydrogen phosphate, potassium dihydrogen phosphate, potassium perchlorate, at least one organic potassium salt selected from the group consisting of potassium carbonate, potassium hydrogen carbonate, potassium salts of aliphatic saturated carboxylic acids such as monocarboxylic acids preferably having from 1 to 6, more preferably from 1 to 5, more preferably from 1 to 4, more preferably from 1 to 3 carbon atoms such as formic acid, acetic acid, propionic acid, dicarboxylic acids preferably having from 2 to 6, more preferably from 2 to 4 carbon atoms such as oxalic acid, malonic acid, succinic acid, tartaric acid, tricarboxylic acids preferably having from 4 to 10 carbon atoms such as citric acid or isocitric acid or propane-1,2,3-tricarboxylic acid, tetracarboxylic acids, and a combination of at least one of the at least one inorganic potassium salts and at least one of the at least one organic potassium salts, the at least one potassium salt more preferably being selected from the group consisting of potassium nitrate, potassium dihydrogen phosphate, potassium formate, and a combination of two or more thereof.

Regarding the concentration of the at least one potassium salt in the liquid mixture provided in (i), no specific restrictions exist. Preferably, the concentration of the at least one potassium salt in the liquid mixture provided in (i) is at least 10%, preferably in the range of from 10 to 100%, preferably from 20 to 100%, more preferably from 30 to 100%, more preferably from 40 to 100% of the solubility limit of the at least one potassium salt in the liquid feed stream provided in (i). The term "solubility limit of the at least one potassium salt in the liquid mixture" as used in the context of the present invention relates to the saturation concentration of the at least one potassium salt in the liquid feed mixture, where by adding more of the at least one potassium salt, the concentration of the at least one potassium salt as solute in the liquid mixture does not increase and at least one of the at least one potassium salt would begin to precipitate. The solubility limit of the at least one potassium salt in the liquid mixture will depend on the composition of the liquid mixture and the conditions such as the temperature at which, and the pressure under which, the liquid mixture is provided in (i). Determining the solubility limit of the at least one potassium salt in the liquid mixture is an easy and straightforward task for the skilled person knowing said conditions and said composition of a given liquid mixture. A simple procedure to evaluate whether the amount of the at least one potassium salt being added is above the solubility limit is passing the liquid mixture through a filter and measure the pressure drop across the filter. If the pressure drop across the filter increases with time on stream and at least one of the at least one potassium salt is found on the filter when it is taken offline, the amount of the at least one potassium salt being added is already above the solubility limit. Therefore, the at least one potassium salt is preferably completely dissolved in the liquid mixture provided in (i).

Therefore, the present invention also relates to the process as defined above, wherein the concentration of the at least one potassium salt in the liquid mixture provided in (I) is at least 10%, preferably in the range of from 10 to 100%, more preferably from 20 to 100%, more preferably from 30 to 100%, more preferably from 40 to 100% of the solubility limit of the at least one potassium salt in the liquid mixture provided in (i).

Therefore, the present invention also relates to the process as described above, comprising (i) providing a liquid mixture comprising the compound of formula (I), hydrogen peroxide, at least one dissolved potassium salt, and optionally a solvent, wherein the concentration of the at least one potassium salt in the liquid mixture provided in (i) is in the range of from 10 to 100% of the solubility limit of the at least one potassium salt in the liquid mixture provided in (i).

Preferably, the molar ratio of potassium, contained in the at least one potassium salt, said at least one potassium salt being contained in the liquid mixture provided in (i), relative to hydrogen peroxide is in the range of from $25\times10^{-6}:1$ to $1000\times10^{-6}:1$, more preferably from $100\times10^{-6}:1$ to $600\times10^{-6}:1$, more preferably from $250\times10^{-6}:1$ to $450\times10^{-6}:1$.

Further preferably, the molar ratio of potassium, contained in the liquid mixture provided in (i), relative to hydrogen peroxide is in the range of from $25\times10^{-6}:1$ to $1000\times10^{-6}:1$, preferably from $100\times10^{-6}:1$ to $600\times10^{-6}:1$, more preferably from $250\times10^{-6}:1$ to $450\times10^{-6}:1$.

Therefore, the present invention also relates to the process as described above, comprising Thus, the present invention also relates to the process as described above, comprising (i) providing a liquid mixture comprising the compound of formula (I), hydrogen peroxide, at least one at least partially dissolved potassium salt, and a polar solvent, wherein the molar ratio of potassium, contained in the liquid mixture provided in (i), relative to hydrogen peroxide is in the range of from $25\times10^{-6}:1$ to $1000\times10^{-6}:1$, preferably from $100\times10^{-6}:1$ to $600\times10^{-6}:1$, more preferably from $250\times10^{-6}:1$ to $450\times10^{-6}:1$.

Thus, the present invention also relates to the process as described above, comprising (i) providing a liquid mixture comprising the compound of formula (I), hydrogen peroxide, at least one at least partially dissolved potassium salt, and a polar solvent selected from the group consisting of acetonitrile, 1,2-dichloroethane, dichloromethane, chloroform, propionitrile, 1,4-dioxane, methyl tert-butyl ether, diethyl ether, dibutyl ether, ethyl acetate, butyl acetate, dimethyl carbonate, ethylene carbonate, propylene carbonate, and mixtures of two or more thereof, the solvent more preferably being 1,2-dichloroethane, 1,4-dioxane, acetonitrile, or a mixture of two or three thereof, wherein for providing the liquid mixture in (i), the hydrogen peroxide is employed in (i) in the form of an aqueous hydrogen peroxide solution having a hydrogen peroxide concentration in the range of from 30 to 80 weight-%, more preferably from 35 to 75 weight-%, more preferably from 40 to 70 weight-%, based on the total weight of the aqueous hydrogen peroxide solution, wherein the aqueous hydrogen peroxide solution further comprises sodium at a molar ratio of sodium relative to hydrogen peroxide in the range of from $1 \times 10^{-6}:1$ to $250 \times 10^{-6}:1$, preferably from $5 \times 10^{-6}:1$ to $50 \times 10^{-6}:1$,
wherein the at least one potassium salt is selected from the group consisting of at least one inorganic potassium salt selected from the group consisting of potassium hydroxide, potassium halides, potassium nitrate, potassium sulfate, potassium hydrogen sulfate, potassium hydrogen phosphate, potassium dihydrogen phosphate, potassium perchlorate, at least one organic potassium salt selected from the group consisting of potassium carbonate, potassium hydrogen carbonate, potassium salts of aliphatic saturated carboxylic acids such as monocarboxylic acids preferably having from 1 to 6, more preferably from 1 to 5, more preferably from 1 to 4, more preferably from 1 to 3 carbon atoms such as formic acid, acetic acid, propionic acid, dicarboxylic acids preferably having from 2 to 6, more preferably from 2 to 4 carbon atoms such as oxalic acid, malonic acid, succinic acid, tartaric acid, tricarboxylic acids preferably having from 4 to 10 carbon atoms such as citric acid or isocitric acid or propane-1,2,3-tricarboxylic acid, tetracarboxylic acids, and a combination of at least one of the at least one inorganic potassium salts and at least one of the at least one organic potassium salts, the at least one potassium salt more preferably being selected from the group consisting of potassium nitrate, potassium dihydrogen phosphate, potassium formate, and a combination of two or more thereof, and
wherein the molar ratio of potassium, contained in the liquid mixture provided in (I), relative to hydrogen peroxide is in the range of from $25 \times 10^{-6}$ 1 to $1000 \times 10^{-6}:1$, preferably from $100 \times 10^{-6}:1$ to $600 \times 10^{-6}:1$, more preferably from $250 \times 10^{-6}:1$ to $450 \times 10^{-6}:1$.

Regarding to concentration of the compound according to formula (I), no specific restrictions exist provided that the reacting according to (ii) can be carried out. Preferably, the liquid mixture provided in (i) contains the compound according to formula (I) at a molar ratio of the hydrogen peroxide relative to the compound according to formula (I) in the range of from 0.1:1 to 5:1, preferably from 0.2 to 1:1, more preferably from 0.3:1 to 0.99:1, more preferably from 0.5:1 to 0.95:1. Therefore, the present invention also relates to the process as described above, wherein at the beginning of the reacting according to (ii), the molar ratio of the hydrogen peroxide relative to the compound according to formula (I) is in the range of from 0.1:1 to 5:1, preferably from 0.2 to 1:1, more preferably from 0.3:1 to 0.99:1, more preferably from 0.5:1 to 0.95:1.

The liquid mixture can be provided in (i) at any desired temperature and at any desired pressure, provided that the mixture is in its liquid form, optionally consisting of one, two or more different liquid phases. Preferably, the liquid mixture is provided having a temperature in the range of from 10 to 50° C., more preferably from 15 to 40° C., more preferably from 20 to 30° C. Preferably, the liquid mixture is provided at a pressure in the range of from 0.7 to 1.5 bar, more preferably from 0.8 to 1.3 bar, more preferably from 0.9 to 1.1° C., more preferably at ambient pressure. Therefore, the present invention also relates to the process as described above, wherein in (i), the liquid mixture is provided having a temperature in the range of from 10 to 50° C., preferably from 15 to 40° C., more preferably from 20 to 30° C., at ambient pressure.

The Tin-containing Zeolitic Material

According to (ii), the compound according to formula (I) is reacted with the hydrogen peroxide in the presence of a catalyst comprising a tin-containing zeolitic material.

Depending on how the reacting in (ii) is carried out, for example in batch mode, semi-continous mode, or continuous mode, the zeolitic material can be employed as such, i.e. as zeolitic powder obtained from the synthesis and an optional post-treatment, or in the form of a molding prepared by subjecting the zeolitic powder obtained from the synthesis and an optional post-treatment to a shaping process from which the molding is obtained which, in addition to the zeolitic powder, may further comprise a binder.

Regarding the zeolitic framework structure of the tin-containing zeolitic material, no specific restrictions exist. Preferably, the tin-containing zeolitic material is a tin-containing zeolitic material having a framework structure selected from the group consisting of ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MMFI, MFS, MON, MOR, MSO, MTF, MTN, MIT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, SIT, TER, THO, TON, TSC, UEI, UFI, UOZ, USI, UTL, VET, VFI, VNI, VSV, WEI, WEN, YUG, ZON, and a mixed framework structure of two or more of these framework structures, or a mixture of two or more of these tin-containing zeolitic materials.

More preferably, the tin-containing zeolitic material is a tin-containing zeolitic material having a framework structure selected from the group consisting of BEA, MWW, and a mixed structure thereof, or a mixture of two or more of these structures.

The term "MWW framework structure" as used in the context of the present invention relates to those zeolitic materials having the MWW structure type which is defined, for example, in Camblor et al. and also those zeolitic structures which are derived from this structure and have a different interlayer distance, indicated by a different lattice parameter c. Preferably, a tin-containing zeolitic material according to the present invention has an X-ray diffraction pattern comprising peaks at 2 theta diffraction angles of $(7.1 \pm 0.1)°$, and $(7.9 \pm 0.1)°$, more preferably an X-ray diffraction pattern comprising peaks at 2 theta diffraction angles of $(7.1 \pm 0.1)°$, $(7.9 \pm 0.1)°$, $(9.6 \pm 0.1)°$, $(12.8 \pm 0.1)°$, $(14.4 \pm 0.1)°$, $(14.7 \pm 0.1)°$, $(15.8 \pm 0.1)°$, $(19.3 \pm 0.1)°$, $(20.1 \pm 0.1)°$, $(21.7 \pm 0.1)°$, $(21.9 \pm 0.1)°$, $(22.6 \pm 0.1)°$, $(22.9 \pm 0.1)°$, $(23.6 \pm 0.1)°$, $(25.1 \pm 0.1)°$, $(26.1 \pm 0.1)°$, $(26.9 \pm 0.1)°$, $(28.6 \pm 0.1)°$, and $(29.1 \pm 0.1)°$.

Preferably, at least a portion if the tin contained in the tin-containing zeolitic material is located at zeolitic framework structure sites. Other elements constituting the zeolitic framework structure which preferably consists of $YO_2$ and $X_2O_3$ preferably include at least one of Si, Ti, Zr, and Ge regarding Y and at least one of Al, B, In, Ga, and Fe regarding X. Therefore, the present invention relates to the process as described above, wherein the tin-containing zeolitic material has a framework structure comprising $X_2O_3$ and $YO_2$, wherein Y is a tetravalent element selected from the group consisting of Si, Ti, Zr, Ge, and combinations of two or more thereof, and X is a trivalent element selected from the group consisting of Al, B, In, Ga, Fe, and combinations of two or more thereof. Preferably, Y is Si, and the tin-containing zeolitic material has a framework structure comprising $X_2O_3$ and $YO_2$, wherein Y is Si and X is a trivalent element selected from the group consisting of Al, B, In, Ga, Fe, and combinations of two or more thereof. Preferably, X is Al and/or B, more preferably B, and the tin-containing zeolitic material has a framework structure comprising $X_2O_3$ and $YO_2$, wherein Y is a tetravalent element selected from the group consisting of Si, Ti, Zr, Ge, and combinations of two or more thereof, and X is a trivalent element selected from the group consisting of Al, B, and combinations of two or more thereof, X more preferably being B. More preferably, Y is Si and X is B, and the tin-containing zeolitic material has a framework structure comprising $X_2O_3$ and $YO_2$, wherein Y is Si and X is B.

Therefore, the present invention relates to the process as described above, wherein the tin-containing zeolitic material is a tin-containing zeolitic material having a framework structure selected from the group consisting of BEA, MWW, and a mixed structure thereof, or a mixture of two or more of these structures, and wherein the framework structure comprises $X_2O_3$ and $YO_2$, wherein Y is Si and X is a trivalent element selected from the group consisting of Al, B, In, Ga, Fe, and combinations of two or more thereof, Y preferably being Si and X preferably being B.

Preferably, tin-containing zeolitic materials are employed wherein at least 95 weight-%, preferably at least 98 weight-%, more preferably at least 99 weight-%, more preferably 99.5 weight-%, more preferably at least 99.8 weight-%, more preferably at least 99.9 weight-% of the zeolitic framework structure consist of $SiO_2$ and $B_2O_3$ and Sn.

The tin-containing zeolitic material employed in the process of the present invention can be prepared by any conceivable process. For example, it is conceivable to prepare the tin-containing zeolitic material from the sources for $X_2O_3$ and $YO_2$, including at least one source for tin, for example in a hydrothermal synthesis process. It is also conceivable to prepare a tin-containing zeolitic material from the sources for $X_2O_3$ and $YO_2$, obtaining a zeolitic material whose framework structure consists of $X_2O_3$ and $YO_2$, and to introduce tin into the zeolitic framework in a suitable post-treatment step, preferably after having formed vacant framework sites, preferably vacant tetrahedral framework sites, in the zeolitic framework. Preferably, the forming of such vacant framework sites, preferably vacant tetrahedral framework sites, can be achieved by treating the zeolitic material whose framework structure consists of $X_2O_3$ and $YO_2$ with acid, with steam, or with a mild solvent system such as water and/or alcohol at suitable conditions. Introducing tin into the zeolitic framework structure can be preferably achieved by hydrothermal treatment of the zeolitic framework having vacant framework sites in the presence of at least one suitable tin source, and optionally in the presence of a zeolitic framework structure directing agent. Introducing tin into the zeolitic framework structure can also be preferably achieved by a solid-state ion-exchange process by suitably mixing the zeolitic framework having vacant framework sites in the presence with at least at least one suitable tin source. If necessary, the thus obtained tin-containing zeolitic material can be subjected to an additional post-treatment stage, for example an impregnation step, preferably a wet-impregnation step, according to which additional tin can be introduced into the zeolitic material, preferably as extra-framework tin.

The tin content of the tin-containing zeolitic material employed in (ii) is not subject to any specific restrictions. Preferably, the tin-containing zeolitic material has a tin content in the range of from 0.1 to 25 weight-%, more preferably from 0.2 to 20 weight-%, more preferably from 0.3 to 16 weight-%, more preferably from 0.4 to 15 weight-%, based on the total weight of the tin-containing zeolitic material.

Regarding the amount of the tin-containing zeolitic material employed in (ii), no specific restrictions exist. Preferably, the amount of catalyst comprising the tin-containing zeolitic material is chosen so that at the beginning of the reacting according to (ii), the weight ratio of the tin-containing zeolitic material relative to hydrogen peroxide is in the range of from 0.01:1 to 5:1, more preferably from 0.05:1 to 4:1, more preferably from 0.1:1 to 3:1.

Preferred processes for the preparation of a tin-containing zeolitic material, and preferred tin-containing zeolitic materials which can be employed in the process of the present invention, are described hereinunder.

According to a preferred process, tin is introduced into a zeolitic material having MWW framework structure and having vacant zeolitic framework sites via hydrothermal treatment of said zeolitic material in the presence of a tin source. The process for the preparation of the tin-containing zeolitic material and the tin-containing zeolitic material are illustrated by the following embodiments and combinations of embodiments as indicated by the respective back-references and dependencies:

1. A process for preparing a tin-containing zeolitic material having an MWW framework structure (Sn-MWW) comprising
   (a) providing a boron-containing zeolitic material having an MWW framework structure comprising $SiO_2$ and $B_2O_3$ (B-MWW);
   (b) deboronating the B-MWW by treating the B-MWW provided in (a) with a liquid solvent system having a pH in the range of from 5.5 to 8;
   (c) incorporating Sn into the deboronated B-MWW obtained from (b) by a process comprising
      (c.1) preparing an aqueous synthesis mixture containing the deboronated B-MWW obtained from (ii), an MWW template compound, preferably selected from the group consisting of piperidine, hexamethylene imine, N,N,N,N',N',N'-hexamethyl-1,5-pentanediammonium ion, 1,4-bis(N-methylpyrrolidinium)butane, octyltrimethylammonium hydroxide, heptyltrimethylammonium hydroxide, hexyltrimethylammonium hydroxide, and a mixture of two or more thereof, and a tin source, wherein in the synthesis mixture, the molar ratio of Sn, calculated as $SnO_2$, relative to Si, calculated as $SiO_2$ and contained in the deboronated B-MWW, is at most 0.015:1;
      (c.2) hydrothermally synthesizing a tin-containing zeolitic material having an MWW-type framework structure from the synthesis mixture obtained from (c.1) thereby obtaining a tin-containing zeolitic material having an MWW-type framework structure in its mother liquor;
      (c.3) separating the tin-containing zeolitic material having an MWW-type framework structure obtained from (c.2) from its mother liquor;
   (d) treating the tin containing zeolitic material having an MWW framework structure obtained from (c) with an aqueous solution having a pH of at most 5 thereby obtaining the Sn-MWW having an Sn content of at most 2 weight-%, calculated as element and based on the weight of the Sn-MWW, and optionally separating the Sn-MWW from the aqueous solution.

2. The process of embodiment 1, wherein in (a), the B-MWW is provided by a process comprising
(a-1) hydrothermally synthesizing a B-MWW precursor from an aqueous synthesis mixture containing a silicon source, preferably ammonia stabilized colloidal silica, a boron source, preferably boric acid, and an MWW template compound, preferably selected from the group consisting of piperidine, hexamethylene imine. N,N,N,N',N',N'-hexamethyl-1,5-pentanediammonium ion, 1,4-bis(N-methylpyrrolidinium)butane, octyltrimethylammonium hydroxide, heptyltrimethylammonium hydroxide, hexyl-trimethylammonium hydroxide, and a mixture of two or more thereof, to obtain the B-MWW precursor in its mother liquor;
(a-2) separating the B-MWW precursor from its mother liquor, preferably comprising drying the B-MWW precursor, wherein the drying is preferably carried out at a temperature in the range of from 100 to 180° C., more preferably from 110 to 140° C.,
wherein in the synthesis mixture in (a-1),
the molar ratio of B, calculated as $B_2O_3$ and contained in the boron source, relative to Si, calculated as $SiO_2$ and contained in the Si source, is preferably in the range of from 0.4:1 to 0.6:1, more preferably from 0.45:1 to 0.55:1, more preferably from 0.47:1 to 0.52:1;
the molar ratio of the MWW template compound, relative to Si, calculated as $SiO_2$ and contained in the Si source, is preferably in the range of from 0.8:1 to 1.7:1, more preferably from 1.0:1 to 1.5:1, more preferably from 1.1:1 to 1.3:1; and
the molar ratio of $H_2O$ relative to Si, calculated as $SiO_2$ and contained in the Si source, is preferably in the range of from 12:1 to 20:1, more preferably from 13:1 to 18:1, more preferably from 14:1 to 16:1.
3. The process of embodiment 2, wherein (a-2) comprises spray-drying the B-MWW precursor.
4. The process of embodiment 2, wherein the drying is carried out for a period in the range of from 1 to 10 h, more preferably from 2 to 6 h.
5. The process of any of embodiments 2 to 4, wherein (a-2) comprises calcination of the separated and preferably dried B-MWW precursor to obtain the B-MWW, wherein the calcination is preferably carried out at a temperature in the range of from 400 to 800° C., more preferably from 600 to 700° C.
6. The process of embodiment 5, wherein the calcination is carried out for a period in the range of from 1 to 10 h, more preferably from 2 to 6 h.
7. The process of any of embodiments 1 to 6, wherein in (a), at least 95 weight-%, preferably at least 98 weight-%, more preferably at least 99 weight-% of the framework structure of the B-MWW consist of $B_2O_3$ and $SiO_2$.
8. The process any of embodiments 1 to 7, wherein in (a), the molar ratio $B_2O_3$:$SiO_2$ of the B-MWW is at least 0.03:1, preferably in the range of from 0.03:1 to 0.09:1, more preferably from 0.03:1 to 0.08:1, more preferably from 0.03:1 to 0.07:1.
9. The process of any of embodiments 1 to 8, wherein in (b), the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water, wherein preferably, the liquid solvent system does not contain an inorganic or organic acid, or a salt thereof.
10. The process of any of embodiments 1 to 9, wherein in (b), the weight ratio of the liquid solvent system relative to B-MWW is in the range of from 40:1 to 5:1, preferably from 30:1 to 7:1, more preferably from 20:1 to 10:1.
11. The process of any of embodiments 1 to 10, wherein in (b), the treating is carried out at a temperature in the range of from 50 to 125° C., preferably from 90 to 115° C. more preferably from 95 to 105° C.
12. The process of any of embodiments 1 to 11, wherein in (b), the treating is carried out for a period in the range of from 6 to 20 h, preferably from 7 to 17 h, more preferably from 8 to 12 h.
13. The process of any of embodiments 1 to 12, wherein in (b), the treating is carried out in a closed system under autogenous pressure.
14. The process of any of embodiments 1 to 12, wherein in (b), the treating is carried out in an open system under reflux.
15. The process of any of embodiments 1 to 14, wherein (b) comprises drying the deboronated B-MWW, the drying preferably being carried out at a temperature in the range of from 100 to 180° C., more preferably from 110 to 140° C.
16. The process of embodiment 15, wherein (b) comprises spray-drying the deboronated B-MWW.
17. The process of embodiment 15, wherein the drying is carried our for a period in the range of from 1 to 30 h, preferably from 14 to 18 h.
18. The process of any of embodiments 1 to 17, wherein (b) comprises calcination of the separated and preferably dried deboronated B-MWW, wherein the calcination is preferably carried out at a temperature in the range of from 400 to 800° C., more preferably from 600 to 700° C.
19. The process of any of embodiments 1 to 18, wherein the deboronated B-MWW has a molar ratio $B_2O_3$:$SiO_2$ of at most 0.01:1, preferably in the range of from 0.001:1 to 0.01:1, more preferably from 0.001:1 to 0.003:1.
20. The process of any of embodiments 1 to 19, wherein the template compound used in (c.1) is piperidine.
21. The process of any of embodiments 1 to 20, wherein the tin source is selected from the group consisting of $SnCl_4$, Sn(IV)-acetate, Sn(IV)-tert-butoxide, $SnBr_4$, $SnCl_4$, $SnF_4$, Sn(IV)-bisacetylacetonate dichloride; Sn(IV)-bisacetylacetonate dibromide, Sn(II)-acetate, Sn(II)acetylacetonate, Sn(II)-citrate, $SnCl_2$, $SnF_2$, $SnI_2$, $SnSO_4$, and a mixture of two or more thereof, the tin source preferably being Sn(IV)-tert-butoxide.
21. The process of any of embodiments 1 to 20, wherein in the synthesis mixture in (c.1), the molar ratio of Sn, calculated as $SnO_2$, relative to Si, calculated as $SiO_2$ and contained in the deboronated B-MWW, is in the range of from 0.001:1 to 0.015:1, preferably from 0.001:1 to 0.010:1, more preferably from 0.001:1 to 0.0075:1, more preferably from 0.001:1 to 0.005:1.
22. The process of any of embodiments 1 to 21, wherein in the synthesis mixture in (c.1), the molar ratio of the MWW template compound relative to Si, calculated as $SiO_2$ and contained in the deboronated B-MWW, is in the range of from 1.0:1 to 2.0:1, preferably from 1.2:1 to 1.8:1, more preferably from 1.4:1 to 1.6:1,
23. The process of any of embodiments 1 to 22, wherein in the synthesis mixture in (c.1), the molar ratio of $H_2O$ relative to Si, calculated as $SiO_2$ and contained in the deboronated B-MWW, is in the range of from 10:1 to 20:1, preferably from 12:1 to 18:1, more preferably from 14:1 to 16:1.
24. The process of any of embodiments 1 to 23, wherein the hydrothermal synthesizing according to (c.2) is carried

19

24. ...out at a temperature in the range of from 80 to 250° C., preferably from 120 to 200° C., more preferably from 160 to 180° C.

25. The process of any of embodiments 1 to 24, wherein the hydrothermal synthesizing according to (c.2) is carried out for a period in the range of from 20 to 200 h, more preferably from 60 to 160 h, more preferably from 110 to 125 h.

26. The process of any of embodiments 1 to 25, wherein (c.3) comprises drying the tin-containing zeolitic material having an MWW framework structure, wherein the drying is preferably carried out at a temperature in the range of from 100 to 180° C., more preferably from 110 to 140° C.

27. The process of embodiment 26, wherein (c.3) comprises spray-drying the tin-containing zeolitic material having an MWW framework structure.

28. The process of embodiment 26, wherein the drying is carried out for a period in the range of from 1 to 30 h, preferably from 6 to 24 h, more preferably from 14 to 18 h.

29. The process of any of embodiments 1 to 28, wherein in (c.3) and before (d), the separated and preferably dried tin-containing zeolitic material having an MWW framework structure is not subjected to calcination.

30. The process of any of embodiments 1 to 29, wherein in (d), the aqueous solution comprises an organic acid, preferably selected from the group consisting of oxalic acid, acetic acid, citric acid, methane sulfonic acid, and a mixture of two or more thereof, and/or an inorganic acid, preferably selected from the group consisting of phosphoric acid, sulphuric acid, hydrochloric acid, nitric acid, and a mixture of two or more thereof, the inorganic acid more preferably being nitric acid.

31. The process of any of embodiments 1 to 30, wherein in (d), the aqueous solution has a pH in the range of from 0 to 5, preferably from 0 to 3, more preferably from 0 to 2.

32. The process of any of embodiments 1 to 31, wherein in (d), the tin-containing zeolitic material having an MWW framework structure is treated with the aqueous solution at a temperature in the range of from 50 to 175° C., preferably from 70 to 125° C., more preferably from 95 to 105° C.

33. The process of any of embodiments 1 to 32, wherein in (d), the tin-containing zeolitic material having an MWW framework structure is treated with the aqueous solution for a period in the range of from 1 to 40 h, more preferably from 12 to 24 h, more preferably from 18 to 22 h.

34. The process of any of embodiments 1 to 33, wherein in (d), the weight ratio of the aqueous solution relative to the tin-containing zeolitic material having an MWW framework structure is in the range of from 10:1 to 50:1, preferably from 20:1 to 40:1, more preferably from 25:1 to 35:1.

35. The process of any of embodiments 1 to 34, wherein in (d), the treating is carried out in a closed system under autogenous pressure.

36. The process of any of embodiments 1 to 34, wherein in (d), the treating is carried out in an open system under reflux.

37. The process of any of embodiments 1 to 36, wherein the tin content of the Sn-MWW obtained from (d), calculated as element and based on the weight of the Sn-MWW, is in the range of from 0.1 to 1.9 weight-%, more preferably from 0.2 to 1.5 weight-%, more preferably from 0.3 to 1.2 weight-%, more preferably from 0.4 to 1.0 weight-%.

20

38. The process of any of embodiments 1 to 37, wherein (d) comprises drying the Sn-MWW, wherein the drying is preferably carried out at a temperature in the range of from 100 to 180° C., more preferably from 110 to 130° C.

39. The process of embodiment 38, wherein (d) comprises spray-drying the Sn-MWW.

40. The process of embodiment 38, wherein the drying is carried out for a period in the range of from 1 to 20 h, preferably from 4 to 16 h, more preferably from 8 to 12 h.

41. The process of any of embodiments 1 to 40, wherein (d) comprises calcination of the preferably separated and preferably dried Sn-MWW, wherein the calcination is preferably carried out at a temperature in the range of from 400 to 800° C., more preferably from 450 to 700° C., more preferably from 500 to 600° C.

42. The process of embodiment 41, wherein the calcination is carried out for a period in the range of from 1 to 20 h, more preferably from 8 to 12 h.

43. A tin containing zeolitic material having an MWW framework structure (Sn-MWW), having a tin content of at most 2 weight-%, calculated as element and based on the weight of the Sn-MWW, and having an X-ray diffraction pattern comprising a peak at a 2 theta diffraction angle of $(6.6\pm0.1)°$, preferably a peak at a 2 theta diffraction angle of $(6.6\pm0.1)°$, a peak at a 2 theta diffraction angle of $(7.1\pm0.1)°$, and a peak at a 2 theta diffraction angle of $(7.9\pm0.1)°$.

44. The zeolitic material of embodiment 43, wherein the zeolitic material has a tin content in the range of from 0.1 to 1.9 weight-%, more preferably from 0.2 to 1.5 weight-%, more preferably from 0.3 to 1.2 weight-%, more preferably from 0.4 to 1.0 weight-%, calculated as element and based on the weight of the Sn-MWW.

45. The zeolitic material of embodiment 43 or 44, having an X-ray diffraction pattern comprising peaks at 2 theta diffraction angles of $(6.6\pm0.1)°$, $(7.1\pm0.1)°$, $(7.9\pm0.1)°$, $(9.6\pm0.1)°$, $(12.8\pm0.1)°$, $(14.4\pm0.1)°$, $(14.7\pm0.1)°$, $(15.8\pm0.1)°$, $(19.3\pm0.1)°$, $(20.1\pm0.1)°$, $(21.7\pm0.1)°$, $(21.9\pm0.1)°$, $(22.6\pm0.1)°$, $(22.9\pm0.1)°$, $(23.6\pm0.1)°$, $(25.1\pm0.1)°$, $(26.1\pm0.1)°$, $(26.9\pm0.1)°$, $(28.6\pm0.1)°$, and $(29.1\pm0.1)°$.

46. The zeolitic material of any of embodiments 43 to 46, wherein the c parameter, as determined via XRD, is $(27.1\pm0.2)$ Angstrom.

47. The zeolitic material of any of embodiments 43 to 46, wherein the MWW framework structure of the Sn-MWW comprises $SiO_2$ and $B_2O_3$ and the molar ratio $B_2O_3:SiO_2$ is at most 0.01:1, preferably in the range of from 0.001:1 to 0.01:1, more preferably from 0.001:1 to 0.003:1.

48. The zeolitic material of any of embodiments 43 to 47, wherein at least 95 weight-%, preferably at least 98 weight-%, more preferably at least 99 weight-% of the MWW framework structure of the Sn-MWW consist of $SiO_2$ and $B_2O_3$ and Sn.

49. The zeolitic material of any of embodiments 43 to 48, having a BET surface area, determined according to DIN 66131, in the range of from 300 to 600 $m^2/g$, preferably from 350 to 550 $m^2/g$.

50. The zeolitic material of any of embodiments 43 to 49, having a Langmuir surface, determined according to DIN 66131, in the range of from 400 to 800 $m^2/g$, preferably from 400 to 750 $m^2/g$.

51. The zeolitic material of any of embodiments 43 to 50, obtainable or obtained by a process according to any of embodiments 1 to 42, or a zeolitic material obtainable or obtained by a process according to any of embodiments 1 to 42.

52. The zeolitic material of any of embodiments 43 to 51 as a spray-powder.

According to a further preferred process, tin is introduced into a zeolitic material having MWW framework structure and having vacant zeolitic framework sites via solid-state ion exchange of said zeolitic material in the presence of a tin source. The process for the preparation of the tin-containing zeolitic material and the tin-containing zeolitic material are illustrated by the following embodiments and combinations of embodiments as indicated by the respective back-references and dependencies:

1. A process for preparing a tin-containing zeolitic material having an MWW framework structure comprising
   (a) providing a zeolitic material having an MWW framework structure comprising $X_2O_3$ and $YO_2$, wherein Y is a tetravalent element selected from the group consisting of Si, Ti, Zr, Ge, and combinations of two or more thereof, and X is a trivalent element selected from the group consisting of Al, B, In, Ga, Fe, and combinations of two or more thereof, said MWW framework structure having vacant tetrahedral framework sites;
   (b) providing a tin-ion source in solid form;
   (c) incorporating tin into the zeolitic material provided in (a) by bringing the zeolitic material provided in (a) in contact with the tin-ion source provided in (b) under solid-state ion exchange conditions, obtaining a tin-containing zeolitic material having an MWW framework structure.
2. The process of embodiment, wherein Y is Si and X is B.
3. The process of embodiment 1 or 2, wherein according to (a), the zeolitic material having an MWW framework structure having vacant tetrahedral framework sites is provided by a method comprising
   (a.1) providing a zeolitic starting material having an MWW framework structure, wherein the framework structure of the zeolitic starting material comprises $X_2O_3$ and $YO_2$ and the molar ratio $X_2O_3:YO_2$ is at least 0.03:1, preferably in the range of from 0.03:1 to 0.09:1, more preferably from 0.03:1 to 0.08:1, more preferably from 0.03:1 to 0.07:1;
   (a.2) creating vacant tetrahedral framework sites by treating the zeolitic starting material provided in (a.1) with a liquid solvent system, preferably under reflux, obtaining a zeolitic material having a molar ratio $X_2O_3:YO_2$ of less than 0.03:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic or organic acid, or a salt thereof, and wherein the treating is preferably carried out at a temperature in the range of from 50 to 125° C., more preferably from 90 to 115° C., more preferably from 95 to 105° C., and preferably for a period in the range of from 6 to 20 h, more preferably from 7 to 17 h, more preferably from 8 to 12 h;
   (a.3) at least partially separating the zeolitic material obtained from (a.2) from the liquid solvent system, optionally including drying, preferably being carried out at a temperature in the range of from 100 to 180° C., more preferably from 110 to 140° C.;
   (a.4) optionally calcining the separated zeolitic material obtained from (a.3), preferably at a temperature in the range of from 400 to 800° C., more preferably from 600 to 700° C.
4. The process of any of embodiments 1 to 3, wherein in the framework structure of the zeolitic material provided in (a), the molar ratio $X_2O_3:YO_2$ is at most 0.01:1, preferably in the range of from 0.001:1 to 0.01:1, more preferably from 0.001:1 to 0.003:1.
5. The process of any of embodiments 1 to 4, wherein at least 95 weight-%, preferably at least 98 weight-%, more preferably at least 99 weight-% of the framework structure of the zeolitic material provided in (a) consist of $X_2O_3$ and $YO_2$.
6. The process of any of embodiments 1 to 5, wherein the tin-ion source provided in (a) is selected from the group consisting of tin(II) alkoxides, tin(IV) alkoxides, tin(II) salts of organic acids, tin(IV) salts of organic acids, and a mixture a two or more thereof, preferably from the group consisting of tin(II) alkoxides having from 1 to 4 carbon atoms, tin(IV) alkoxides having from 1 to 4 carbon atoms, tin(II) salts of organic acids having from 1 to 6, tin(IV) salts of organic acids having from 1 to 6 carbon atoms, and a mixture a two or more thereof, wherein more preferably, the tin-ion source provided in (ii) is tin(II) acetate.
7. The process of any of embodiments 1 to 6, wherein according to (c), the molar ratio of tin contained in the tin-ion source brought into contact with zeolitic material relative to the vacant tetrahedral framework sites of the zeolitic material is at most 1:1.
8. The process of any of embodiments 1 to 7, wherein in (c), bringing the zeolitic material provided in (a) in contact with the tin-ion source provided in (b) under solid-state ion exchange conditions comprises mixing the zeolitic material provided in (a) together with the tin-ion source.
9. The process of embodiment 8, wherein in (c), the zeolitic material is mixed with the tin-ion source for a time period in the range of from 2 min to 5 h, preferably from 5 min to 3 h, more preferably from 10 min to 2 h.
10. The process of embodiment 8 or 9, wherein the milling is carried out under stirring at a stirring energy input min the range of from 100 to 1000 W, preferably from 200 to 800 W, more preferably from 300 to 600 W.
11. The process of any embodiments 8 to 10, comprising grinding and/or milling the zeolitic material prior to milling the zeolitic material together with the tin-ion source, or grinding and/or milling the tin-ion source prior to milling the zeolitic material together with the tin-ion source, or grinding and/or milling the zeolitic material prior to milling the zeolitic material together with the tin-ion source and grinding and/or milling the tin-ion source prior to milling the zeolitic material together with the tin-ion source.
12. The process of any of embodiments 1 to 11, further comprising
   (iv) subjecting the zeolitic material obtained from (c) to a heat-treatment.
13. The process of embodiment 12, wherein the heat-treating according to (d) comprises drying and the drying is carried out at a temperature in the range of from 75 to 175° C., preferably from 100 to 150° C., for a time period in the range of from 2 to 48 h, more preferably from 6 to 24 h, preferably at least partially in an atmosphere comprising oxygen.
14. The process of embodiment 12 or 13, wherein the heat-treating according to (d) comprises calcining and the calcining is carried out at a temperature in the range of from 400 to 700° C., preferably from 450 to 600° C., for a time period in the range of from 1 to 10 h, more preferably from 2 to 8 h, preferably at least partially in an atmosphere comprising oxygen.
15. The process of any of embodiments 1 to 14, further comprising
   (e) treating the zeolitic material obtained from (c) or (d), preferably from (d), with an aqueous solution having a pH of at most 5.
16. The process of any of embodiments 1 to 15, wherein in (e), the aqueous solution comprises an organic acid, preferably selected from the group consisting of oxalic acid, acetic acid, citric acid, methane sulfonic acid, and a mixture of two or more thereof, and/or comprises an inorganic acid, preferably selected from the group consisting of phosphoric acid, sulphuric acid, hydrochloric acid, nitric acid, and a mixture of two or more thereof, the inorganic acid more preferably being nitric acid.
17. The process of embodiment 15 or 16, wherein in (e), the aqueous solution has a pH in the range of from 0 to 5, preferably from 0 to 3.5, more preferably from 0 to 2.
18. The process of any of embodiments 15 to 17, wherein in (e), the zeolitic material is treated with the aqueous solution at a temperature in the range of from 70° C. to 100° C., preferably from 80° C. to 100° C., more preferably from 90 to 100° C., preferably in a closed system under autogenous pressure.
19. The process of any of embodiments 15 to 18, wherein in (e), the zeolitic material is treated with the aqueous solution for a time period in the range of from 10 min to 40 h, preferably from 30 min to 30 h, more preferably from 1 h to 25 h.
20. The process of any of embodiments 15 to 19, wherein in (e), the zeolitic material is treated with the aqueous solution at a weight ratio of the aqueous solution relative to the zeolitic material in the range of from 2:1 to 50:1, preferably from 8:1 to 40:1, more preferably from 10:1 to 35:1.
21. The process of any of embodiments 15 to 20, further comprising
   (vi) drying and calcining the zeolitic material obtained (e), preferably after washing, wherein the drying is preferably carried out at a temperature in the range of from 90° C. to 180° C., preferably from 100° C. to 150° C., fore period in the range of from 1 h to 24 h, preferably from 6 h to 12 h, and the calcining is preferably carried out at a temperature in the range of from 400 to 700° C., preferably from 450 to 600° C., for a period in the range of from 1 h to 24 h, preferably from 6 h to 12 h.
22. A tin-containing zeolitic material, obtainable or obtained by a process according to any of embodiments 1 to 21.
23. A tin-containing zeolitic material having an MWW-type framework structure comprising $X_2O_3$ and $YO_2$, wherein Y is a tetravalent element selected from the group consisting of Si, Ti, Zr, Ge, and combinations of two or more thereof, Y preferably being Si, X is a trivalent element selected from the group consisting of Al, B, In, Ga, Fe, and combinations of two or more thereof. X preferably being B, wherein the framework structure additionally comprises tin, wherein in the framework structure of the zeolitic material, the molar ratio $X_2O_3:YO_2$ is at most 0.01:1, preferably in the range of from 0.001:1 to 0.01:1, more preferably from 0.001:1 to 0.003:1, wherein at least 95 weight-%, preferably at least 98 weight-%, more preferably at least 99 weight-% of the framework structure of the zeolitic material consist of X, Y, O, and tin, and wherein the tin-containing zeolitic material has a tin content of at least 10 weight-%, based on the total weight of the tin-containing zeolitic material.
24. The tin-containing zeolitic material of embodiment 23, having a tin content in the range of from 10 to 20 weight-%, preferably from 11 to 18 weight-%, more preferably from 12 to 16 weight-%, based on the total weight of the tin-containing zeolitic material.
25. The tin-containing zeolitic material of embodiment 23 or 24, obtainable or obtained by a process according to any of claims 1 to 21.

According to a further preferred process, tin is introduced into a zeolitic material having BEA framework structure and having vacant zeolitic framework sites via solid-state ion exchange of said zeolitic material in the presence of a tin source. The process for the preparation of the tin-containing zeolitic material and the tin-containing zeolitic material are illustrated by the following embodiments and combinations of embodiments as indicated by the respective back-references and dependencies:

1. A process for preparing a tin-containing zeolitic material having a BEA framework structure comprising
   (a) providing a zeolitic material having a BEA framework structure comprising $X_2O_3$ and $YO_2$, wherein Y is a tetravalent element selected from the group consisting of Si, Ti, Zr, Ge, and combinations of two or more thereof, and X is a trivalent element selected from the group consisting of Al, B, In, Ga, Fe, and combinations of two or more thereof, said BEA framework structure having vacant tetrahedral framework sites;
   (b) providing a tin-ion source in solid form;
   (c) incorporating tin into the zeolitic material provided in (a) by bringing the zeolitic material provided in (a) in contact with the tin-ion source provided in (b) under solid-state ion exchange conditions, obtaining a tin-containing zeolitic material having a BEA framework structure;
   (d) subjecting the zeolitic material obtained from (c) to a heat treatment;
   (e) treating the het-treated zeolitic material obtained from (d) with an aqueous solution having a pH of at most 5.
2. The process of claim 1, wherein Y is Si and X is B.
3. The process of embodiment 1 or 2, wherein according to (a), the zeolitic material having a BEA framework structure having vacant tetrahedral framework sites is provided by a method comprising
   (a.1) providing a zeolitic starting material having a BEA framework structure, wherein the framework structure of the zeolitic starting material comprises $X_2O_3$ and $YO_2$ and the molar ratio $X_2O_3:YO_2$ is greater than 0.02:1, preferably at least 0.03:1, more preferably in the range of from 0.03:1 to 0.07:1, more preferably from 0.03:1 to 0.06:1, more preferably from 0.03:1 to 0.05:1;
   (a.2) creating vacant tetrahedral framework sites by treating the zeolitic starting material provided in (a.1) with a liquid solvent system, preferably under reflux, obtaining a zeolitic material having a molar ratio $X_2O_3:YO_2$ of at most 0.02:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic or organic acid, or a salt thereof, and wherein the treating is preferably carried out at a temperature in the range of from 50 to 125° C., more preferably from 90 to 115° C., more preferably from 95 to 105° C., preferably for a period in the range of from 6 to 20 h, more preferably from 7 to 17 h, more preferably from 8 to 12 h;
- (a.3) at least partially separating the zeolitic material obtained from (a.2) from the liquid solvent system, optionally including drying;
- (a.4) optionally calcining the separated zeolitic material obtained from (a.3), preferably at a temperature in the range of from 400 to 700° C., more preferably from 450 to 550° C., and preferably for a time period in the range of from 1 to 10 h, more preferably from 3 to 6 h.

4. The process of any of embodiments 1 to 3, wherein in the framework structure of the zeolitic material provided in (a), the molar ratio $X_2O_3:YO_2$ is at most 0.02:1, preferably at most 0.01:1, more preferably in the range of from 0.0005:1 to 0.01:1, more preferably from 0.0009:1 to 0.003:1.

5. The process of any of embodiments 1 to 4, wherein at least 95 weight-%, preferably at least 98 weight-%, more preferably at least 99 weight-% of the framework structure of the zeolitic material provided in (a) consist of $X_2O_3$ and $YO_2$.

6. The process of any of embodiments 1 to 5, wherein the tin-ion source provided in (b) is selected from the group consisting of tin(II) alkoxides, tin(IV) alkoxides, tin(II) salts of organic acids, tin(IV) salts of organic acids, and a mixture a two or more thereof, preferably from the group consisting of tin(II) alkoxides having from 1 to 4 carbon atoms, tin(IV) alkoxides having from 1 to 4 carbon atoms, tin(II) salts of organic acids having from 1 to 6, tin(IV) salts of organic acids having from 1 to 6 carbon atoms, and a mixture a two or more thereof, wherein more preferably, the tin-ion source provided in (b) is tin(II) acetate.

7. The process of any of embodiments 1 to 6, wherein according to (c), the molar ratio of tin contained in the tin-ion source brought into contact with zeolitic material relative to the vacant tetrahedral framework sites of the zeolitic material is at most 1:1

8. The process of any of embodiments 1 to 7, wherein in (c), bringing the zeolitic material provided in (a) in contact with the tin-ion source provided in (b) under solid-state ion exchange conditions comprises mixing the zeolitic material provided in (a) with the tin-ion source.

9. The process of embodiment 8, wherein in (c), the zeolitic material is mixed with the tin-ion source for a time period in the range of from 2 min to 5 h, preferably from 5 min to 3 h, more preferably from 10 min to 2 h.

10. The process of embodiment 8 or 9, wherein the mixing is carried out under stirring at a stirring energy input min the range of from 100 to 1000 W, preferably from 200 to 800 W, more preferably from 300 to 600 W.

11. The process of any embodiments 8 to 10, comprising grinding and/or milling the zeolitic material prior to milling the zeolitic material together with the tin-ion source, or grinding and/or milling the tin-ion source prior to milling the zeolitic material together with the tin-ion source, or grinding and/or milling the zeolitic material prior to milling the zeolitic material together with the tin-ion source and grinding and/or milling the tin-ion source prior to milling the zeolitic material together with the tin-ion source.

12. The process of any of embodiments 1 to 11, wherein the heat-treating according to (d) comprises calcining, wherein the calcining is preferably carried out at a temperature in the range of from 400 to 700° C., more preferably from 450 to 650° C., more preferably from 500 to 600° C., preferably for a time period in the range of from 1 to 10 h, more preferably from 2 to 8 h, more preferably from 3 to 6 hours, preferably at least partially in an atmosphere comprising oxygen.

13. The process of any of embodiments 1 to 12, wherein the calcining according to (d) is partially carried out in an inert gas atmosphere.

14. The process of any of embodiments 1 to 13, wherein in (e), the aqueous solution comprises an organic acid, preferably selected from the group consisting of oxalic acid, acetic acid, citric acid, methane sulfonic acid, and a mixture of two or more thereof, and/or comprises an inorganic acid, preferably selected from the group consisting of phosphoric acid, sulphuric acid, hydrochloric acid, nitric acid, and a mixture of two or more thereof, the inorganic acid more preferably being nitric acid.

15. The process of any of embodiments 1 to 14, wherein in (e), the aqueous solution has a pH in the range of from 0 to 5, preferably from 0 to 3.5, more preferably from 0 to 2.

16. The process of any of embodiments 1 to 15, wherein in (e), the heat-treated material is treated with the aqueous solution at a temperature in the range of from 20 to 130° C., preferably from 50 to 120° C., more preferably from 90 to 110° C.

17. The process of any of embodiments 1 to 16, wherein in (e), the heat-treated zeolitic material is treated with the aqueous solution for a time period in the range of from 10 min to 40 h, preferably from 30 min to 30 h, more preferably from 1 h to 25 h.

18. The process of any of embodiments 1 to 17, wherein in (e), the heat-treated zeolitic material is treated with the aqueous solution at a weight ratio of the aqueous solution relative to the heat-treated zeolitic material in the range of from 2:1 to 50:1, preferably from 8:1 to 40:1, more preferably from 10:1 to 35:1.

19. The process of any of embodiments 1 to 18, further comprising
- (f) drying and/or calcining the zeolitic material obtained from (e), optionally after washing, wherein the drying is preferably carried out at a temperature in the range of from 100 to 180° C., preferably from 120 to 150° C., for a period in the range of from 10 to 70 h, preferably from 15 to 25 h, and calcination is preferably carried out at a temperature in the range of from 550 to 700° C., preferably from 600 to 680° C., for a period in the range of from 1 to 10 h, preferably from 2 to 5 h.

20. A tin-containing zeolitic material having a BEA framework structure comprising $X_2O_3$ and $YO_2$, wherein Y is a tetravalent element selected from the group consisting of Si, Ti, Zr, Ge, and combinations of two or more thereof, Y preferably being Si, X is a trivalent element selected from the group consisting of Al, B, In, Ga, Fe, and combinations of two or more thereof, X preferably being B, wherein the framework structure additionally comprises tin, wherein in the framework structure of the zeolitic material, the molar ratio $X_2O_3:YO_2$, preferably $B_2O_3:SiO_2$, is at most 0.02:1, preferably at most 0.01:1, more preferably in the range of from 0.0005:1 to 0.01:1, more preferably from 0.0009:1 to 0.003:1, wherein at least 95 weight-%, preferably at least 98 weight-%, more preferably at least 99 weight-% of the framework structure of the zeolitic material consist of X, Y, O, and tin, preferably of B, Si, O, and tin, and wherein the tin-containing zeolitic material has a water uptake of at most 12 weight-%, preferably at most 10 weight-%.

21. The tin-containing zeolitic material of embodiment 20, having a tin content in the range of from 2 to 20 weight-%, preferably from 5 to 18 weight-%, more preferably from 8 to 16 weight-%, based on the total weight of the tin-containing zeolitic material.
22. The tin-containing zeolitic material of embodiment 20 or 21, having a UV/Vis spectrum exhibiting a maximum in the range of from 200 to 220 nm.
23. The tin-containing zeolitic material of any of embodiments 20 to 22, obtainable or obtained by a process according to any of claims 1 to 19.

Preparation of Moldings

Depending on the mode according to which the oxidation process of the present invention is carried out in (ii), the catalyst comprising the tin-containing zeolitic material is preferably employed as a powder, a spray-powder, or a molding. For example, if the oxidation process of the present invention is carried out in batch mode, it may be preferred to employ the catalyst comprising the tin-containing zeolitic material as powder or spray-powder. For example, if the oxidation process of the present invention is carried out in semi-continuous mode or continuous mode, it may be preferred to employ the catalyst comprising the tin-containing zeolitic material as spray-powder or as molding. Therefore, depending on the specific mode of the oxidation process of the present invention, it is conceivable that the tin-containing zeolitic powder or the spray-powder, preferably the tin-containing zeolitic powder or the spray-powder according to the above-described embodiments, are further processed to prepare a molding comprising the powder or the spray-powder.

Preferably, the moldings are prepared by a process comprising
(A) preparing a moldable mixture comprising the tin-containing zeolitic material, the moldable mixture optionally comprising a binder or a binder precursor;
(B) subjecting the mixture obtained from (A) to shaping to obtain a molding containing the tin-containing zeolitic material;
(C) optionally drying and/or calcining the molding obtained in (B).

In general, suitable binders are all compounds which impart adhesion and/or cohesion between the zeolitic material particles to be bonded which goes beyond the physisorption which may be present without a binder. Examples of such binders are metal oxides, such as, for example, $SiO_2$, $Al_2O_3$, $TiO_2$, $ZrO_2$ or MgO or clays or mixtures of two or more of these oxides or mixed oxides of at least two of Si, Al, Ti, Zr, and Mg. Clay minerals and naturally occurring or synthetically produced alumina, such as, for example, alpha-, beta-, gamma-, delta-, eta-, kappa-, chi- or theta-alumina and their inorganic or organo-metallic precursor compounds, such as, for example, gibbsite, bayerite, boehmite or pseudoboehmite or trialkoxyaluminates, such as, for example, aluminum triisopropylate, are particularly preferred as $Al_2O_3$ binders. Further conceivable binders might be amphiphilic compounds having a polar and a non-polar moiety and graphite. Further binders might be, for example, clays, such as, for example, montmorillonites, kaolins, metakaolin, hectorite, bentonites, halloysites, dickites, nacrites or anaxites. These binders can be used as such or in the form of suitable precursor compounds which, either during spray-drying and/or the subsequent calcination form the desired binder. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate. In the context of the present invention binders which either completely or partly comprise $SiO_2$, or which are a precursor of $SiO_2$, from which $SiO_2$ is formed, are preferred. In this context, both colloidal silica and so-called "wet process" silica and so-called "dry process" silica can be used. This silica may be amorphous silica, the size of the silica particles being, for example, in the range of from 5 to 100 nm and the surface area of the silica particles being in the range of from 50 to 500 $m^2$/g. Colloidal silica, preferably as an alkaline and/or ammoniacal solution, more preferably as an ammoniacal solution, is commercially available, inter alia, for example as Ludox®, Syton®, Nalco® or Snowtex®. "Wet process" silica is commercially available, inter alia, for example as Hi-Sil®, Ultrasil®, Vulcasil®, Santocel®, Valron-Estersil®, Tokusil® or Nipsil®. "Dry process" silica is commercially available, inter alia, for example as Aerosil®, Reolosil®, Cab-O-Sil®, Fransil® or ArcSilica®. Inter alia, an ammoniacal solution of colloidal silica can be preferred.

As to the ratio of the amount of the tin-containing zeolitic material relative to the amount of the binder used for preparing a molding, it generally can be freely chosen. Generally, the weight ratio of the tin-containing zeolitic material relative to the binder is in the range of from 20:1 to 1:20, preferably from 10:1 to 1:10, more preferably from 1:1 to 1:10.

For preparing a molding based on the tin-containing zeolitic material, at last one pasting agent can be used to provide for an improved processability of the moldable mixture. Conceivable pasting agents are, among others, organic, in particular hydrophilic polymers, such as, for example, carbohydrates like cellulose, cellulose derivatives, such as, for example, methyl cellulose, and starch, such as, for example, potato starch, wallpaper plaster, polyacrylates, polymethacrylates, polyvinyl alcohol, polyvinylpyrrolidone, polyisobutene or polytetrahydrofuran. The use of water, alcohols or glycols or mixtures thereof, such as mixtures of water and alcohol, or water and glycol, such as for example water and methanol, or water and ethanol, or water and propanol, or water and propylenglycol, as pasting agents may be mentioned. Preferably, carbohydrates such as cellulose, cellulose derivatives, water and mixtures of two or more of these compounds, such as water and cellulose or water and cellulose derivatives are used as pasting agent. In a particularly preferred embodiment of the process according to the invention, the at least one pasting agent is removed by drying and/or calcination, as further described below. Such pasting agents may be also used as compounds imparting a specific porosity, preferably a mesoporosity, to the moldings.

As to the ratio of the amount of the tin-containing zeolitic material relative to the amount of the pasting agent used for preparing a molding, it generally can be freely chosen. Generally, the weight ratio of the tin-containing zeolitic material relative to the pasting agent is in the range of from 20:1 to 1:50, preferably from 10:1 to 1:40, more preferably from 1:1 to 1:30.

It is further conceivable that a pore-forming agent, in particular a mesopore-forming agent is additionally employed for the preparation of the moldings. Such pore forming agents usually employed are preferably polymeric vinyl compounds, such as, for example, polyalkylene oxides, such as polyethylene oxides, polystyrene, polyacrylates, polymethacrylates, polyolefins, polyamides and polyesters.

As to the ratio of the amount of the tin-containing zeolitic material relative to the amount of the pore-forming agent used for preparing a molding, it generally can be freely chosen. Generally, the weight ratio of the tin-containing zeolitic material relative to the pore-forming agent is in the range of from 20:1 to 1:50, preferably from 10:1 to 1:40, more preferably from 1:1 to 1:30.

The moldings of the present invention may be shaped in (B) in every conceivable geometry such as strands, for example having rectangular, triangular hexagonal, quadratic, oval, or circular cross-section, stars, tablets, spheres, hollow cylinders, and the like. Depending on the specific geometry, the shaping process according to (B) will be chosen. If, according to a preferred embodiment of the present invention, strands are prepared, the shaping according to (B) preferably comprises subjecting the mixture obtained in (A) to extrusion. Suitable extrusion apparatuses are described, for example, in "Ullmann's Enzyklopädie der Technischen Chemie", 4th edition, vol. 2, page 295 et seq., 1972. In addition to the use of an extruder, an extrusion press can also be used for the preparation of the moldings. If necessary, the extruder can be suitably cooled during the extrusion process. Extrusion processes are conceivable wherein per batch, the power consumption is in the range of from 1 to 10 A, preferably from 1.5 to 6 A, more preferably from 2 to 4 A. The strands leaving the extruder via the extruder die head can be mechanically cut by a suitable wire or via a discontinuous gas stream.

The molding obtained from (B) is optionally dried and/or calcined. No specific restrictions exist concerning the drying and calcination conditions. The drying is preferably carried out at temperatures in the range of in general from 80 to 160° C., more preferably from 90 to 155° C., more preferably from 100 to 150° C., and preferably for a duration in the range of from 6 to 24 h, more preferably from 10 to 20 h. The drying can be effected under any suitable gas atmosphere, wherein nitrogen, air and/or lean air are preferred.

The calcination is preferably carried out at temperatures in the range of in general from 400 to 650° C., more preferably from 450 to 625° C., more preferably from 500 to 600° C., and preferably for a duration in the range of from 0.25 to 6 h, more preferably from 0.5 to 25. The calcination can be effected under any suitable gas atmosphere, wherein air and/or lean air are preferred.

Further, it is conceivable that the moldings comprising the tin-containing zeolitic material obtained from (B) or (C), preferably from (C), are subjected to a treatment with an aqueous system having a pH in the range of 5.5 to 8.

Preferably, the moldings are treated with the aqueous system at a temperature in the range of from 80 to 220° C., preferably from 100 to 180° C., more preferably from 130 to 150° C. Further, the treating with the aqueous system is carried out for a period in the range of from 1 to 20 h, preferably from 4 to 15 h, more preferably from 6 to 10 h. Preferably, at least 95 weight-%, more preferably at least 99 weight-%, more preferably at least 99.9 weight-% of the aqueous system consists of water. More preferably, the aqueous system is water.

According to a preferred embodiment of the present invention, the treating with the aqueous system is carried out in a closed system, under autogenous pressure and with or without stirring. According to another embodiment of the present invention, the treating with the aqueous system is carried out in an open system, preferably under reflux, and with or without stirring.

After treating of the moldings with the aqueous system, the moldings are preferably suitably separated from the suspension. All methods of separating the moldings from the suspension are conceivable. These methods include, for example, filtration and centrifugation methods. A combination of two or more of these methods can be applied. According to the present invention, the moldings are preferably separated from the aqueous system by filtration, and the thus obtained moldings are preferably subjected to washing, preferably to washing with water, at a temperature in the range of from up to 50° C., preferably from 15 to 35° C., more preferably from 20 to 30° C.

After treating with the aqueous system, the moldings are preferably subjected to drying and/or calcination, wherein drying is preferably carried out at a temperature in the range of from 100 to 180° C., preferably from 130 to 150° C., for a period in the range of from 10 to 70 h, preferably from 15 to 25 h, and calcination is preferably carried out at a temperature in the range of from 550° C. to 700° C., preferably from 600 to 680° C., for a period in the range of from 1 to 10 h, preferably from 2 to 5 h.

Therefore, the moldings can prepared by a process comprising
(A) preparing a moldable mixture comprising the tin-containing zeolitic material, the moldable mixture optionally comprising a binder or a binder precursor;
(B) subjecting the mixture obtained from (A) to shaping to obtain a molding containing the tin-containing zeolitic material;
(C) optionally drying and/or calcining the molding obtained in (B);
(D) treating the moldings obtained from (B) or (C), preferably (C), with an aqueous system having a pH in the range of 5.5 to 8;
(E) optionally drying and/or calcining the moldings obtained from (D).

The Reacting According to (ii)

The reaction conditions applied in (ii) are not specifically restricted. In particular, concerning the temperature of the reaction mixture according to (ii), no specific restrictions exist, provided that it is suitable to obtain the oxidized organic carbonyl compound of formula (II). In particular, the reaction temperature will depend on the presence or absence of a solvent or the chemical nature of the solvent. Preferably, the reaction according to (i) is carried out at a temperature in the range of from 50 to 150° C., preferably from 70 to 120° C., more preferably from 90 to 110° C.

As described above, the reacting in (ii) can be carried out, for example, in batch mode or in continuous mode. If the reacting according to (ii) is carried out in batch mode, the term "at the beginning of the reaction" relates to the point in time where all starting materials, including the catalyst, are simultaneously present in the reaction mixture and, depending on the temperature, the conversion of the compound of formula (I) begins. If the reaction according to (ii) is carried out in continuous mode, the term "at the beginning of the reaction" relates to the entrance of the reactor through which the reaction mixtures is passed, where the feed stream or the feed streams fed into the reactor get in contact with the catalyst.

According to an embodiment of the present invention, the reacting according to (ii) is carried out in batch mode. No specific restrictions exist concerning the reaction time which is employed, provided that it is suitable to obtain the oxidized organic carbonyl compound of formula (II). Preferably, the reaction is carried out for a period in the range of from 1 to 10 h, preferably from 3 to 5 h. Preferably, the reaction according to (i) is carried out under reflux. In this case, the suitable reaction zone used in (i) is preferably a vessel equipped with suitable heating means equipped with a reflux condenser. Thus, the reacting according to (ii) is preferably carried out in an open system under reflux. During the reaction according to (ii), it is preferred to stir the reaction mixture. The stirring rate can be kept essentially constant or changed during (ii). The stirring rates can be suitably chosen depending, for example, on the volume of the reaction mixture, the desired temperature, and the like.

If the reacting in (ii) is carried out in batch mode, it is preferred that the catalyst is employed in (ii) as a powder or a spray powder, wherein preferably at least 90 weight-%, more preferably at least 95 weight-%, more preferably at least 99 weight-%, more preferably at least 99.5 weight-%, more preferably at least 99.9 weight-% of the catalyst consist of the tin-containing zeolitic material.

According to an embodiment of the present invention, the reaction according to (i) is carried out in continuous mode. No specific restrictions exist concerning the set-up of the continuous process. Preferred continuous process set-ups include the use of at least one fixed-bed reactor wherein the fixed catalyst bed contains the moldings comprising the tin-containing zeolitic material as described above, through which fixed bed the reaction mixture is passed. According to this embodiment, it is possible to feed the individual starting materials, optionally also the solvent, as individual stream into the reactor. It is also possible to suitably combine the individual starting material streams before they are fed to the reactor. For example, it is conceivable to combine the hydrogen peroxide stream with the solvent stream or a portion of the solvent stream and feed this stream to the reactor, wherein the feed containing the compound of formula (I) is fed as separate stream to the reactor, optionally combined with a portion of the solvent stream. It is also conceivable to prepare a single feed stream from individual streams, one stream containing the preferably aqueous hydrogen peroxide, one stream containing the organic compound of formula (I), one optional stream containing the solvent. Generally, it is conceivable that the at least one potassium salt is fed, preferably as aqueous solution, as individual stream to the reactor. Preferably, the at least one potassium salt is fed, contained in the preferably aqueous hydrogen peroxide stream, to the reactor.

Two or more reactors can be employed wherein at least two reactors can be coupled in parallel and/or at least two reactors can be coupled in series. Between two reactors coupled in series, at least one intermediate stage can be realized where, for example, the compound of formula (I) is suitably separated from the reaction mixture and the remaining portion of the reaction mixture, optionally together with one or more fresh starting materials, is fed to the next reactor. If two or more reactors are employed, the catalysts in the reactors can be the same or different from each other provided that they comprise tin-containing zeolitic material.

Therefore, the present invention also relates to the process as described above, carried out in continuous mode, wherein in (i), the liquid mixture is provided as a liquid feed stream comprising the compound of formula (I), hydrogen peroxide, the at least one at least partially dissolved potassium salt, and optionally the solvent, and wherein in (ii), the liquid feed stream provided in (i) is passed into an oxidation reactor comprising the catalyst comprising a tin-containing zeolitic material, and subjecting the liquid feed stream to oxidation reaction conditions in the oxidation reactor, obtaining a reaction mixture comprising the compound of formula (II), at least a portion of the at least one potassium salt, optionally the compound of formula (I), and optionally the solvent, the process preferably comprising removing an effluent stream from the oxidation reactor, the effluent stream comprising the compound of formula (II), at least a portion of the at least one potassium salt, optionally the compound of formula (I), and optionally the solvent.

If the reacting in (ii) is carried out in continuous mode, it is preferred that the catalyst is employed in (ii) as a molding comprising the tin-containing zeolitic material and preferably a binder, wherein the tin-containing zeolitic material is comprised in the molding preferably as powder or spray-powder, wherein preferably at least 90 weight-%, more preferably at least 95 weight-%, more preferably at least 99 weight-%, more preferably at least 99.5 weight-%, more preferably at least 99.9 weight-% of the powder or spray-powder consist of the tin-containing zeolitic material.

After the reaction according to (ii), the used catalyst comprising the tin-containing zeolitic material is separated from the reaction mixture. If the reaction is carried out in continuous mode, preferably using a fixed-bed reactor, the reaction mixture leaves the reactor and the catalyst remains in the reactor. If the reaction is carried out in batch-mode, the separation of the catalyst which is preferably employed as powder or spray-powder comprising the tin-containing zeolitic material can be achieved by any conceivable method including, for example, filtration, ultrafiltration, diafiltration and centrifugation and/or decantation methods, wherein filtration methods can involve suction and/or pressure filtration steps.

After separation, the separated catalyst is optionally subjected to one or more washing steps using one or more suitable washing agents. Conceivable washing agents may include water, ethers such as dioxanes such as 1,4-dioxane, alcohols such as methanol, ethanol, propanol, or mixtures of two or more thereof. Preferred washing agents are dioxanes. Preferred temperatures applied during the washing step are in the range of from 10 to 50° C., preferably from 15 to 40° C., more preferably from 20 to 30° C.

Generally, the present invention also relates to a reaction mixture, obtainable or obtained from step (ii) of the process as described above, optionally after separation of the catalyst.

Step (iii)

After the reacting according to (ii), the obtained compound of formula (II) is preferably separated from the reaction mixture obtained from (ii). Therefore, the present invention relates to the process described above, wherein the process further comprises (iii) separating the compound of formula (II) from the mixture obtained in (i).

In this context, it is conceivable that the reaction mixture obtained from (ii), after separation of the catalyst, is subjected to at least one distillation stage from which the compound of formula (II) is obtained.

Depending on the nature of the solvent, optionally used in (ii), it is conceivable that prior to the distillation, a phase separation is performed and the phase containing the compound of formula (II) is subjected to distillation.

The Catalytic System

According to the present invention, it was found that the specific combination of a catalyst comprising a tin-containing zeolitic material, preferably a tin-containing zeolitic material having MWW or BEA framework structure, and at least one potassium salt which is employed as additive to the catalyst leads to unexpected and superior characteristics of the oxidation reaction where the organic compound according to formula (II) is prepared from the organic compound of formula (I) with hydrogen peroxide as oxidation agent, and preferably in the presence of a solvent. Therefore, the present invention also relates to a catalytic system comprising a catalyst comprising a tin-containing zeolitic material and at least one potassium salt, wherein the at least one potassium salt is selected from the group consisting of at least one inorganic potassium salt, at least one organic potassium salt, and combinations of at least one inorganic potassium salt and at least one organic potassium salt.

The term "catalytic system" as used in this context of the present invention relates to the system comprised of the catalyst comprising a tin-containing zeolitic material, and the at least one potassium salt which catalytic system is realized when the liquid mixture provided in (I) is brought in contact with the catalyst in (ii). This catalytic system is characterized by the following embodiments and combinations of embodiments resulting from the dependencies and back-references as indicated:

1. A catalytic system comprising a catalyst comprising a tin-containing zeolitic material and at least one potassium salt, wherein the at least one potassium salt is selected from the group consisting of at least one inorganic potassium salt, at least one organic potassium salt, and combinations of at least one inorganic potassium salt and at least one organic potassium salt.
2. The catalytic system of embodiment 1, wherein the at least one potassium salt is selected from the group consisting of at least one inorganic potassium salt selected from the group consisting of potassium hydroxide, potassium halides, potassium nitrate, potassium sulfate, potassium hydrogen sulfate, potassium hydrogen phosphate, potassium dihydrogen phosphate, potassium perchlorate, at least one organic potassium salt selected from potassium carbonate, potassium hydrogen carbonate, potassium salts of aliphatic saturated carboxylic acids such as monocarboxylic acids preferably having from 1 to 6, more preferably from 1 to 5, more preferably from 1 to 4, more preferably from 1 to 3 carbon atoms such as formic acid, acetic acid, propionic acid, dicarboxylic acids preferably having from 2 to 6, more preferably from 2 to 4 carbon atoms such as oxalic acid, malonic acid, succinic acid, tartaric acid, tricarboxylic acids preferably having from 4 to 10 carbon atoms such as citric acid or isocitric acid or propane-1,2,3-tricarboxylic acid, tetracarboxylic acids, and a combination of at least one of the at least one inorganic potassium salts and at least one of the at least one organic potassium salts.
3. The catalytic system of embodiment 1 or 2, wherein the at least one potassium salt is selected from the group consisting of potassium nitrate, potassium dihydrogen phosphate, potassium formate, and a combination of two or more thereof.
4. The catalytic system of any of embodiments 1 to 3, wherein the tin-containing zeolitic material is a tin-containing zeolitic material having a framework structure selected from the group consisting of ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MMFI, MFS, MON, MOR, MSO, MTF, MTN, MTT, MTW, MWW, NAB, NAT, NES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI, VNI, VSV, WEI, WEN, YUG, ZON, and a mixed framework structure of two or more of these framework structures, or a mixture of two or more of these tin-containing zeolitic materials, preferably a tin-containing zeolitic material having a framework structure selected from the group consisting of BEA, MWW, and a mixed framework structure of these framework structures, or a or a mixture of these tin-containing zeolitic materials.
5. The catalytic system of any of embodiments 1 to 4, wherein the tin-containing zeolitic material has a tin content in the range of from 0.1 to 25 weight-%, more preferably from 0.2 to 20 weight-%, more preferably from 0.3 to 16 weight-%, more preferably from 0.4 to 15 weight-%, based on the total weight of the tin-containing zeolitic material.
6. The catalytic system of any of embodiments 1 to 5, wherein at least 95 weight-%, preferably at least 98 weight-%, more preferably at least 99 weight-%, more preferably 99.5 weight-%, more preferably at least 99.8 weight-%, more preferably at least 99.9 weight-% of the zeolitic framework structure consist of $SiO_2$ and $B_2O_3$ and Sn.
7. The catalytic system of any of embodiments 1 to 6, wherein the catalyst is the tin-containing zeolitic material in the form of a powder or spray-powder, or is a molding comprising the tin-containing zeolitic material and preferably a binder, wherein the tin-containing zeolitic material is comprised in the molding preferably as powder or spray-powder, wherein preferably at least 90 weight-%, more preferably at least 95 weight-%, more preferably at least 99 weight-%, more preferably at least 99.5 weight-%, more preferably at least 99.9 weight-% of the powder or spray-powder consist of the tin-containing zeolitic material.
8. The catalytic system of any of embodiments 1 to 7 for the oxidation of an organic carbonyl compound of formula (I)

wherein $R_1$ and $R_2$ are independently from one another a linear or branched alkyl residue, a linear or branched alkenyl residue, an aryl or heteroaryl residue, or a hydrogen atom with the proviso that $R_1$ and $R_2$ are not simultaneously a hydrogen atom.
9. The catalytic system of embodiment 8, wherein neither $R_1$ nor $R_2$ is a hydrogen atom and $R_1$ and $R_2$ form, together with the carbonyl group in the compound of formula (I), a ring, preferably having from 4 to 20, more preferably from 4 to 18, more preferably from 5 to 16, such as 5, 6, 7, 8, 9, 10, 11, 12, 13, 14, 15, or 16 carbon atoms, preferably 5, 6, 8, 12, 15 or 16 carbon atoms.
10. The catalytic system of embodiment 8 or 9, wherein the compound of formula (I) is selected from the group consisting of cyclopentanone, cyclohexanone, cycloheptanone, cyclooctanone, cyclododecanone, cyclopentadecanone, cyclohexadecanone, 2-pentylcyclopentanone, 2-heptylcyclopentanone, cyclohexadec-8-en-1-one, and a mixture of two or more thereof.

11. The catalytic system of any of embodiments 1 to 10, being obtainable or obtained by a process comprising
(i') providing a liquid mixture comprising hydrogen peroxide, the at least one potassium salt, optionally a solvent, and a compound of formula (I)

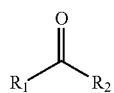

(I)

wherein $R_1$ and $R_2$ are independently from one another a linear or branched alkyl residue, a linear or branched alkenyl residue, an aryl or heteroaryl residue, or a hydrogen atom with the proviso that $R_1$ and $R_2$ are not simultaneously a hydrogen atom, and
wherein the liquid mixture contains the catalyst comprising a tin-containing zeolitic material;
(ii') preferably reacting the compound of formula (I) with the hydrogen peroxide in the liquid mixture in the presence of the catalyst comprising a tin-containing zeolitic material, obtaining a compound of formula (II)

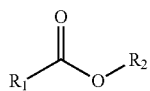

(II)

wherein, if neither $R_1$ nor $R_2$ is a hydrogen atom, $R_1$ and $R_2$ may form, together with the carbonyl group or the carboxyl group, a ring and the compound of formula (I) is

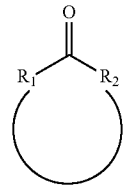

and the compound of formula (II) is

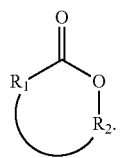

12. The catalytic system of embodiment 11, wherein the molar ratio of potassium relative to hydrogen peroxide in the liquid mixture provided in (i') is in the range of from $25 \times 10^{-6}:1$ to $1000 \times 10^{-6}:1$, preferably from $100 \times 10^{-6}:1$ to $600 \times 10^{-6}:1$, more preferably from $250 \times 10^{-6}:1$ to $450 \times 10^{-6}:1$.

13. The catalytic system of embodiment 11 or 12, wherein the concentration of the at least one potassium salt in the liquid mixture provided in (i') is at least 10%, more preferably in the range of from 10 to 100%, more preferably from 20 to 100%, more preferably from 30 to 100%, more preferably from 40 to 100% of the solubility limit of the at least one potassium salt in the liquid mixture provided in (i').

14. The catalytic system of any of embodiments 11 to 13, wherein in (i'), a solvent is comprised in the liquid mixture, said solvent preferably being a polar solvent, more preferably a polar aprotic solvent, said solvent more preferably being selected from the group consisting of acetonitrile, 1,2-dichloroethane, dichloromethane, chloroform, propionitrile, 1,4-dioxane, methyl tert-butyl ether, diethyl ether, dibutyl ether, ethyl acetate, butyl acetate, dimethyl carbonate, ethylene carbonate, propylene carbonate, and mixtures of two or more thereof, the solvent more preferably being 1,2-dichloroethane, 1,4-dioxane, acetonitrile, or a mixture of two or three thereof.

Generally, the present invention also relates to the use of at least one potassium salt as an additive for a catalyst comprising a tin-containing zeolitic material in a process for the oxidation of an organic carbonyl compound of formula (I)

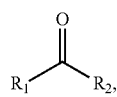

(I)

or to a process for the oxidation of an organic carbonyl compound of formula (I) wherein at least one potassium salt is employed as an additive for a catalyst comprising a tin-containing zeolitic material,
wherein $R_1$ and $R_2$ are independently from one another a linear or branched alkyl residue, a linear or branched alkenyl residue, an aryl or heteroaryl residue, or a hydrogen atom with the proviso that $R_1$ and $R_2$ are not simultaneously a hydrogen atom, preferably with hydrogen peroxide as epoxidation agent, obtaining a compound of formula (II)

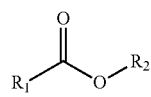

(II)

wherein, if neither $R_1$ nor $R_2$ is a hydrogen atom, $R_1$ and $R_2$ may form, together with the carbonyl group or the carboxyl group, a ring and the compound of formula (I) is

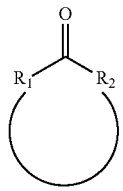

and the compound of formula (II) is

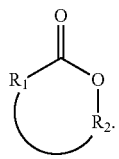

Further, the present invention relates to said use or said process, wherein the tin-containing zeolitic material is a tin-containing zeolitic material having a framework structure selected from the group consisting of ABW, ACO, AEI, AEL, AEN, AET, AFG, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MMFI, MFS, MON, MOR, MSO, MTF, MTN, MIT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, SIT, TER, THO, TON, TSC, UEI, UFI, UOZ, USI, UTL, VET, VFI, VNI, VSV, WEI, WEN, YUG, ZON, and a mixed framework structure of two or more of these framework structures, or a mixture of two or more of these tin-containing zeolitic materials, preferably a tin-containing zeolitic material having a framework structure selected from the group consisting of BEA, MWW, and a mixed framework structure of these framework structures, or a mixture of two or more of these tin-containing zeolitic materials, and wherein the tin-containing zeolitic material has a tin content in the range of from 0.1 to 25.0 weight-%, preferably from 0.2 to 20 weight-%, more preferably from 0.3 to 16 weight-%, more preferably from 0.4 to 15 weight-%.

Yet further, the present invention relates to said use or said process, wherein the at least one potassium salt is selected from the group consisting of at least one inorganic potassium salt selected from the group consisting of potassium hydroxide, potassium halides, potassium nitrate, potassium sulfate, potassium hydrogen sulfate, potassium hydrogen phosphate, potassium dihydrogen phosphate, potassium perchlorate, at least one organic potassium salt selected from potassium carbonate, potassium hydrogen carbonate, potassium salts of aliphatic saturated carboxylic acids such as monocarboxylic acids preferably having from 1 to 6, more preferably from 1 to 5, more preferably from 1 to 4, more preferably from 1 to 3 carbon atoms such as formic acid, acetic acid, propionic acid, dicarboxylic acids preferably having from 2 to 6, more preferably from 2 to 4 carbon atoms such as oxalic acid, malonic acid, succinic acid, tartaric acid, tricarboxylic acids preferably having from 4 to 10 carbon atoms such as citric acid or isocitric acid or propane-1,2,3-tricarboxylic acid, tetracarboxylic acids, and a combination of at least one of the at least one inorganic potassium salts and at least one of the at least one organic potassium salts.

The present invention is further illustrated by the following reference examples, comparative examples, and examples.

EXAMPLES

Reference Example A

Determination of the Water Uptake

The water uptake of the zeolitic materials is determined by water adsorption/desorption isotherms which were performed on a VTI SA instrument from TA Instruments following a step-isotherm program. The experiment consisted of a run or a series of runs performed on a sample material that has been placed on the microbalance pan inside of the instrument. Before the measurement was started, the residual moisture of the sample was removed by heating the sample to 100° C. (heating ramp of 5° C./min) and holding it for 6 h under a nitrogen flow. After the drying program, the temperature in the cell was decreased to 25° C. and kept isothermal during the measurement. The microbalance was calibrated, and the weight of the dried sample was balanced (maximum mass deviation 0.01 weight-%). Water uptake by the sample was measured as the increase in weight over that of the dry sample. First, as adsorption curve was measured by increasing the relative humidity (RH) (expressed as weight-% water in the atmosphere inside of the cell) to which the sample was exposed and measuring the water uptake by the sample as equilibrium. The RH was increased with a step of 10 weight-% from 5% to 85% and at each step the system controlled the RH and monitored the sample weight until reaching the equilibrium conditions after the sample was exposed from 85 weight-% to 5 weight-% with a step of 10% and the change in the weight of the sample (water uptake) was monitored and recorded.

Reference Example B

Determination of the Crystallinity

B.1 Crystallinity of Zeolitic Materials Having MWW Framework Structure

The crystallinity of the zeolitic materials according to the present invention was determined by XRD analysis. The data are collected using a standard Bragg-Brentano diffractometer with a Cu-X-ray source and an energy dispersive point detector. The angular range of 2° to 70° (2 theta) is scanned with a step size of 0.02°, while the variable divergence slit is set to a constant illuminated sample length of 20 mm. The data are then analyzed using TOPAS V4 software, wherein the sharp diffraction peaks are modeled using a Pawley fit containing a unit cell with the following starting parameters: a=14.4 Angstrom and c=25.2 Angstrom in the space group P6/mmm. These are refined to fit the data. A linear background is modelled. Independent peaks are inserted at the following positions. 8.4°, 22.4°, 28.2° and 43°. These are used to describe the amorphous content. The crystalline content describes the intensity of the crystalline signal to the intensity to the amorphous content.

B.2 Crystallinity of Zeolitic Materials Having BEA Framework Structure

The crystallinity of the zeolitic materials according to the present invention was determined by XRD analysis using the EVA method as described in the User Manual DIFFRAC.EVA Version 3, page 105, from Bruker AXS GmbH, Karlsruhe. The respective data were collected on a standard Bruker D8 Advance Diffractometer Series II using a Sol-X detector, from 2° to 50° 2theta, using variable slits (V20), a step size of 0.02° 2theta and a scan speed of 2.4 s/step.

Default parameters were used for estimating the background/amorphous content (Curvature=1, Threshold=1).

Reference Example C

FT-IR Measurements

The FT-IR (Fourier-Transformed-Infrared) measurements were performed on a Nicolet 6700 spectrometer. The powdered material was pressed into a self-supporting pellet without the use of any additives. The pellet was introduced into a high vacuum (HV) cell placed into the FT-IR instrument. Prior to the measurement the sample was pretreated in high vacuum ($10^{-5}$ mbar) for 3 h at 300° C. The spectra were collected after cooling the cell to 50° C. The spectra were recorded in the range of 4000 to 800 cm$^{-1}$ at a resolution of 2 cm$^{-1}$. The obtained spectra are represented in a plot having on the x axis the wave-number (cm$^{-1}$) and on the y axis the absorbance (arbitrary units, a.u.). For the quantitative determination of the peak heights and the ratio between these peaks a baseline correction was carried out. Changes in the 3000-3900 cm$^{-1}$ region were analyzed and for comparing multiple samples, as reference the band at 1880±5 cm$^{-1}$ was taken.

Reference Example 1

Preparation of Tin-Containing Zeolitic Materials Having MWW Framework Structure

Reference Example 1.1

Preparation of Tin-Containing Zeolitic Materials Having MWW Framework Structure Via Incorporation of Tin by Hydrothermal Synthesis Reference Example 1.1.1

Preparation of a Tin-Containing Zeolitic Material Having MWW Framework Structure and Having a Sn Content of 0.46 Weight-% Via Incorporation of Tin by Hydrothermal Synthesis (i) Preparation of a B-MWW 480 kg de-ionized water were provided in a vessel. Under stirring at 70 rpm (rounds per minute), 166 kg boric acid were suspended in the water at room temperature. The suspension was stirred for another 3 h at room temperature. Subsequently, 278 kg piperidine were added, and the mixture was stirred for another hour. To the resulting solution, 400 kg Ludox® AS-40 were added, and the resulting mixture was stirred at 70 rpm for another hour at room temperature. The finally obtained mixture was transferred to a crystallization vessel and heated to 170° C. within 5 h under autogenous pressure and under stirring (50 rpm). The temperature of 170° C. was kept essentially constant for 120 h. During these 120 h, the mixture was stirred at 50 rpm. Subsequently, the mixture was cooled to a temperature of from 50-60° C. The aqueous suspension containing B-MWW precursor had a pH of 11.3 as determined via measurement with a pH-sensitive electrode. From said suspension, the B-MWW precursor was separated by filtration. The filter cake was then washed with de-ionized water at room temperature until the washing water had a conductivity of less than 700 microSiemens/cm. The thus obtained filter cake was subjected to spray-drying in a spray-tower with the following spray-drying conditions:

| drying gas, nozzle gas: | technical nitrogen |
|---|---|
| temperature drying gas: | |
| temperature spray tower (in): | 235° C. |
| temperature spray tower (out): | 140° C. |
| nozzle: | |
| top-component nozzle: | supplier Gerig; size 0 |
| nozzle gas temperature: | room temperature |
| nozzle gas pressure: | 1 bar |
| operation mode: | nitrogen straight |
| apparatus used: | spray tower with one nozzle |
| configuration: | spray tower - filter - scrubber |
| gas flow: | 1,500 kg/h |
| filter material: | Nomex ® needle-felt 20 m$^2$ |
| dosage via flexible tube pump: | SP VF 15 (supplier: Verder) |

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material was then subjected to calcination at 600° C. for 10 h. The calcined material had a molar ratio $B_2O_3$:$SiO_2$ of 0.06:1.

(ii) Deboronation 9 kg of de-ionized water and 600 g of the calcined zeolitic material obtained according to Example 1 (i) were refluxed at 100° C. under stirring at 250 r.p.m. for 10 h. The resulting deboronated zeolitic material was separated from the suspension by filtration and washed with 4 l deionized water at room temperature. After the filtration, the filter cake was dried at a temperature of 120° C. for 16 h. The dried zeolitic material having an MWW framework structure had a $B_2O_3$:$SiO_2$ molar ratio of 0.0020:1.

(iii) Incorporation of Sn 776.25 g deionized water were provided in a glass beaker and 375 g piperidine were added under stirring. To this suspension 1.45 g of Sn(OAc)$_2$ (Sn(II) acetate) was added and the suspension stirred for another 10 minutes. 172.4 g zeolitic material obtained according to (ii) were added to the mixture and stirred for 20 min (200 r.p.m.) at room temperature. The obtained suspension was than filled in an autoclave. The mixture was treated for 48 h at a temperature of 170° C. under stirring (100 r.p.m.). Afterwards the autoclave was cooled down to room temperature and the resulting zeolitic material was separated from the suspension by filtration at room temperature and washed with deionized water until the washing water had a conductivity of less than 200 microSiemens/cm. After the filtration, the filter cake was dried at a temperature of 120° C. for 16 h. The dried zeolitic material had a Si content of 40 weight-% and a Sn content of 0.42 weight-%.

(iv) Acid Treatment 173.4 g zeolitic material obtained according to (iii) were provided in a round bottom flask and 5,202 g of a 30 weight-% HNO$_3$ aqueous solution, having a pH in the range from 0 to 1, were added. The mixture was stirred at a temperature of 100° C. for a period of 20 h (200 r.p.m.) under reflux. The suspension was filtered and the filter cake was then washed with de-ionized water at room temperature until the washing water had a pH of approximately 7. The obtained zeolitic material was dried at 120° C. for 16 h and calcined by heating to 550° C. (2° C. per minute) and subsequent heating at 550° C. for 10 h. The dried and calcined zeolitic material hat a Si content of 47 weight-% and a Sn content of 0.46 weight-% and a c parameter as determined via XRD of 26.91 Angstrom. The crystallinity of the zeolitic material determined according to XRD was 89%. Further, the zeolitic material had a BET surface area, determined according to DIN 66131 of 520 m$^2$/g, and a Langmuir surface, determined according to DIN 66131 of 713 m$^2$/g. Furthermore, the obtained zeolitic material had a X-ray diffraction pattern comprising peaks at 2 theta diffraction angles of (6.6±0.1)°, (7.1±0.1)°, (7.9±0.1)°, (9.6±0.1)°, (12.8±0.1)°, (14.4±0.1)°, (14.7±0.1)°, (15.8±0.1)°, (19.3±0.1)°, (20.1±0.1)°, (21.7±0.1)°, (21.9±0.1)°, (22.6±0.1)°, (22.9±0.1)°, (23.6±0.1)°, (25.1±0.1)°, (26.1±0A)°, (26.9±0.1)°, (28.6±0A)°, and (29.1±0.1)°.

Reference Example 1.1.2

Preparation of a Tin-Containing Zeolitic Material Having MWW Framework Structure and Having a Sn Content of 0.46 Weight-% Via Incorporation of Tin by Hydrothermal Synthesis, and Preparation of a Molding (i) Preparation of B-MWW 480 kg de-ionized water were provided in a vessel. Under stirring at 70 rpm (rounds per minute), 166 kg boric acid were suspended in the water at room temperature. The suspension was stirred for another 3 h at room temperature. Subsequently, 278 kg piperidine were added, and the mixture was stirred for another hour. To the resulting solution, 400 kg Ludox® AS-40 were added, and the resulting mixture was stirred at 70 rpm for another hour at room temperature. The finally obtained mixture was transferred to a crystallization vessel and heated to 170° C. within 5 h under autogenous pressure and under stirring (50 rpm). The temperature of 170° C. was kept essentially constant for 120 h. During these 120 h, the mixture was stirred at 50 rpm. Subsequently, the mixture was cooled to a temperature of from 50-60° C. The aqueous suspension containing B-MWW had a pH of 11.3 as determined via measurement with a pH-sensitive electrode. From said suspension, the B-MWW was separated by filtration. The filter cake was then washed with de-ionized water at room temperature until the washing water had a conductivity of less than 500 microSiemens/cm. The thus obtained filter cake was subjected to spray-drying in a spray-tower with the following spray-drying conditions:

| drying gas, nozzle gas: | technical nitrogen |
|---|---|
| temperature drying gas: | |
| temperature spray tower (in): | 235° C. |
| temperature spray tower (out): | 140° C. |
| nozzle: | |
| top-component nozzle | supplier Gerig; size 0 |
| nozzle gas temperature: | room temperature |
| nozzle gas pressure: | 1 bar |
| operation mode: | nitrogen straight |
| apparatus used: | spray tower with one nozzle |
| configuration: | spray tower - filter - scrubber |
| gas flow: | 1,500 kg/h |
| filter material: | Nomex ® needle-felt 20 m$^2$ |
| dosage via flexible tube pump: | SP VF 15 (supplier: Verder) |

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material was then subjected to calcination at 650° C. in a rotary oven in contra current flow (0.8-1 kg/h). The calcined material had a B content of 1.4 weight-%, a Si content of 43 wt. %, and TOC of less than 0.1 wt. %. The material had a BET specific surface area, measured according to DIN 66131, of 468 m$^2$/g.

(ii) Deboronation 1,590 kg of de-ionized water and 106 kg of the calcined material obtained from (i) were refluxed at 100° C. under stirring at 70 r.p.m. for 10 h. The resulting deboronated zeolitic material was separated from the suspension by filtration and washed 4 times with 150 l deionized water at room temperature. After the filtration, the filter cake was dried at a temperature of 120° C. for 16 h. The dried zeolitic material having an MWW framework structure had a B content of 0.04 weight-%, a Si content of 42 weight-%, and a BET specific surface area, measured according to DIN 66131, of 462 m$^2$/g.

(iii) Incorporation of Sn 776.25 g deionized water were provided in a glass beaker and 375 g piperidine were added under stirring. To this suspension 2.5 g of Sn(IV)butoxyde pre-dissolved in 25 g piperidine were added and the suspension was stirred for another 10 minutes. 172.4 g deboronated zeolitic material obtained according to (ii) above were added to the mixture and stirred for 60 min (200 r.p.m.) at room temperature. The obtained suspension was than filled in an autoclave. The mixture was treated for 120 h at a temperature of 170° C. under stirring (100 r.p.m.). Afterwards the autoclave was cooled down to room temperature and the resulting zeolitic material was separated from the suspension by filtration at room temperature and washed with deionized water until the washing water had a conductivity of less than 200 microSiemens/cm. After the filtration, the filter cake was dried at a temperature of 120° C. for 16 h. The dried zeolitic material had a Si content of 40 weight-% and a Sn content of 0.42 weight-%.

(iv) Acid Treatment 174 g tin containing zeolitic material obtained from (iii) above were provided in a round bottom flask and 5,220 kg of a 30 weight-% HNO$_3$ aqueous solution, having a pH in the range from 0 to 1, were added. The mixture was stirred at a temperature of 100° C. for a period of 20 h (200 r.p.m.). The suspension was filtered and the filter cake was then washed with de-ionized water at room temperature until the washing water had a pH of approximately 7. The obtained zeolitic material was dried at 120° C. for 16 h and calcined by heating to 550° C. (2 K/min) and subsequent heating at 550° C. for 10 h. The dried and calcined zeolitic material had a Si content of 49 weight-% and a Sn content of 0.46 weight-% and a c parameter as determined via XRD of 27.1 Angstrom. The crystallinity of the zeolitic material determined according to XRD was 86%. Further, the zeolitic material had a BET surface area, determined according to DIN 66131, of 521 m$^2$/g, a Langmuir surface, determined according to DIN 66131 of 695 m$^2$/g.

(v) Preparation of a Molding 140 g of the zeolitic calcined zeolitic material obtained from (iv) and 8.4 g Walocel were kneaded for 5 min in an edge mill. During kneading, 82.6 g Ludox® AS-40 were added continuously. After 10 min, the addition of 150 ml de-ionized water was started. After another 30 min, die kneading mass was adjusted by addition of 30 ml de-ionized water. After a total kneading time of 50 min, the mass is extrudable, and the mass was extruded at a pressure of from 100 to 150 bar during 1 min. The obtained strands were dried at 120° C. for 8 h in an oven and calcined at 500° C. for 5 h. 137.2 g of white strands were obtained, having a diameter of 1.7 mm. The dried and calcined material in the form of said strands had a Si content of 46 weight-%, a Sn content of 0.41 weight-% and TOC of 0.01 weight-%. The crystallinity of the zeolitic material determined according to XRD was 78%. Further, the strands had a BET surface area, determined according to DIN 66131, of 412 m$^2$/g, and a pore volume determined by Hg porosimetry of 0.91 ml/g.

Reference Example 1.2

Preparation of Tin-Containing Zeolitic Materials Having MWW Framework Structure Via Incorporation of Tin by Solid-State Ion Exchange Reference Example 1.2.1

Preparation of a Tin-Containing Zeolitic Material Having MWW Framework Structure and Having a Sn Content of 12.8 Weight-% Via Incorporation of Tin by Solid-State Ion Exchange (i) Preparation of B-MWW 480 kg de-ionized water were provided in a vessel. Under stirring at 70 rpm (rounds per minute), 166 kg boric acid were suspended in the water at room temperature. The suspension was stirred for another 3 h at room temperature. Subsequently, 278 kg piperidine were added, and the mixture was stirred for another hour. To the resulting solution, 400 kg Ludox® AS-40 were added, and the resulting mixture was stirred at 70 rpm for another hour at room temperature. The finally obtained mixture was transferred to a crystallization vessel and heated to 170° C. within 5 h under autogenous pressure and under stirring (50 r.p.m.). The temperature of 170° C. was kept essentially constant for 120 h. During these 120 h, the mixture was stirred at 50 rpm. Subsequently, the mixture was cooled to a temperature of from 50-60° C. The aqueous suspension containing B-MWW had a pH of 11.3 as determined via measurement with a pH-sensitive electrode. From said suspension, the B-MWW was separated by filtration. The filter cake was then washed with de-ionized water at room temperature until the washing water had a conductivity of less than 500 microSiemens/cm. The thus obtained filter cake was subjected to spray-drying in a spray-tower with the following spray-drying conditions:

| drying gas, nozzle gas: | technical nitrogen |
|---|---|
| temperature drying gas: | |
| temperature spray tower (in): | 235° C. |
| temperature spray tower (out): | 140° C. |
| nozzle: | |
| top-component nozzle | supplier Gerig; size 0 |
| nozzle gas temperature: | room temperature |
| nozzle gas pressure: | 1 bar |

-continued

| operation mode: | nitrogen straight |
|---|---|
| apparatus used: | spray tower with one nozzle |
| configuration: | spray tower - filter - scrubber |
| gas flow: | 1,500 kg/h |
| filter material: | Nomex ® needle-felt 20 m$^2$ |
| dosage via flexible tube pump: | SP VF 15 (supplier: Verder) |

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material was then subjected to calcination at 650° C. in a rotary oven in countercurrent flow (0.8-1 kg/h). The calcined material had a B content of 1.4 weight-%, a Si content of 43 weight-%, and a TOC (total organic carbon) of less than 0.1 weight-%. The crystallinity of the material, as determined via XRD, was 88%, and the BET specific surface area measured according to DIN 66131 was 468 m$^2$/g.

(ii) Deboronation 1590 kg of de-ionized water and 106 kg of the calcined material obtained according 2.1 above were refluxed at 100° C. under stirring at 70 r.p.m. for 10 h. The resulting deboronated zeolitic material was separated from the suspension by filtration and washed 4 times with 150 l deionized water at room temperature. After the filtration, the filter cake was dried at a temperature of 120° C. for 16 h. The dried zeolitic material having an MWW-type framework structure had a B content of 0.04 weight-%, a Si content of 42 weight-%, a crystallinity determined via XRD of 82% and a BET specific surface area of 462 m$^2$/g.

(iii) Incorporation of Sn 30 g of the deboronated zeolitic material obtained according to (ii) were added in a Mixer (mill type Microton MB550) together with 8.9 g Sn(OAc)$_2$ (tin(II) acetate, CAS-Nr:638-39-1, Sigma-Aldrich). The two components were milled together for 15 minutes with a stirring rate of 14,000 r.p.m. (rounds per minute). Afterwards, 10.8 g of the thus obtained powder were transferred to a porcelain holder and dried at 120° C. for 10 h.

(iv) Acid Treatment 330 g of nitric acid (30 weight-%) and 11 g of the dried zeolitic material obtained from (iii) were added under stirring in a 0.5 l glass round bottom flask. The mixture in the vessel was heated to 100° C. and kept at this temperature under autogenous pressure for 20 h under stirring (200 r.p.m.). The thus obtained mixture was then cooled within 1 h to a temperature of less than 50° C. The cooled mixture was subjected to filtration, and the filter cake was washed with deionized water until a pH of 7 was reached. The filter cake was dried for 10 h at 120° C. and calcined at 550° C. for 10 h (heating ramp 2 K/min). A zeolitic material was obtained having a Sn content of 12.6 weight-%, a Si content of 36.5 weight-% and a TOC of less than 0.1 weight-%. The BET specific surface area determined according to DIN 66131 was 385 m$^2$/g, and the crystallinity determined according to XRD was 87%.

Reference Example 1.2.2

Preparation of a Tin-Containing Zeolitic Material Having MWW Framework Structure and Having a Sn Content of 12.3 Weight-% Via Incorporation of Tin by Solid-State Ion Exchange (i) Preparation of B-MWW 480 kg de-ionized water were provided in a vessel. Under stirring at 70 rpm (rounds per minute), 166 kg boric acid were suspended in the water at room temperature. The suspension was stirred for another 3 h at room temperature. Subsequently, 278 kg piperidine were added, and the mixture was stirred for another hour. To the resulting solution, 400 kg Ludox® AS-40 were added, and the resulting mixture was stirred at 70 rpm for another hour at room temperature. The finally obtained mixture was transferred to a crystallization vessel and heated to 170° C. within 5 h under autogenous pressure and under stirring (50 r.p.m.). The temperature of 170° C. was kept essentially constant for 120 h. During these 120 h, the mixture was stirred at 50 rpm. Subsequently, the mixture was cooled to a temperature of from 50-60° C. The aqueous suspension containing B-MWW had a pH of 11.3 as determined via measurement with a pH-sensitive electrode. From said suspension, the B-MWW was separated by filtration. The filter cake was then washed with de-ionized water at room temperature until the washing water had a conductivity of less than 500 microSiemens/cm. The thus obtained filter cake was subjected to spray-drying in a spray-tower with the following spray-drying conditions:

| drying gas, nozzle gas: | technical nitrogen |
| --- | --- |
| temperature drying gas: | |
| temperature spray tower (in): | 235° C. |
| temperature spray tower (out): | 140° C. |
| nozzle: | |
| top-component nozzle | supplier Gerig; size 0 |
| nozzle gas temperature: | room temperature |
| nozzle gas pressure: | 1 bar |
| operation mode: | nitrogen straight |
| apparatus used: | spray tower with one nozzle |
| configuration: | spray tower - filter - scrubber |
| gas flow: | 1,500 kg/h |
| filter material: | Nomex ® needle-felt 20 m$^2$ |
| dosage via flexible tube pump: | SP VF 15 (supplier: Verder) |

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material was then subjected to calcination at 650° C. in a rotary oven in countercurrent flow (0.8-1 kg/h). The calcined material had a B content of 1.4 weight-%, a Si content of 43 weight-%, and a TOC (total organic carbon) of less than 0.1 weight-%. The crystallinity of the material, as determined via XRD, was 88%, and the BET specific surface area measured according to DIN 66131 was 468 m$^2$/g.

(ii) Deboronation 1590 kg of de-ionized water and 106 kg of the calcined material obtained according to (i) were refluxed at 100° C. under stirring at 70 r.p.m. for 10 h. The resulting deboronated zeolitic material was separated from the suspension by filtration and washed 4 times with 150 l deionized water at room temperature. After the filtration, the filter cake was dried at a temperature of 120° C. for 16 h. The dried zeolitic material having an MWW-type framework structure had a B content of 0.04 weight-%, a Si content of 42 weight-%, a crystallinity determined via XRD of 82% and a BET specific surface area of 462 m$^2$/g.

(iii) Incorporation of Sn 120 g of the deboronated zeolitic material obtained according to (ii) were added in a Mixer (mill type Microton MB550) together with 34 g Sn(OAc)$_2$ (tin(II) acetate, CAS-Nr:638-39-1, Sigma-Aldrich). The two components were milled together for 15 minutes with a stirring rate of 14,000 r.p.m. (rounds per minute). Afterwards, 28 g of the thus obtained powder were transferred to a porcelain holder and calcined in a static oven for 3 h at 500° C., heating rate 2 K/min. The calcined powder had the following elemental composition: Sn 11.5 weight-%, Si 35 weight-% and TOC of less than 0.1 weight-%. The BET specific surface area determined according to DIN 66131 was 392 m$^2$/g, and the crystallinity determined via XRD was 79%.

(iv) Acid Treatment 1800 g of nitric acid (30 weight-%) and 60 g of the calcined zeolitic material obtained from (iii) were added under stirring in a 2.0 l glass round bottom flask. The mixture in the vessel was heated to 100° C. and kept at this temperature under autogenous pressure for 20 h under stirring (200 r.p.m.). The thus obtained mixture was then cooled within 1 h to a temperature of less than 50° C. The cooled mixture was subjected to filtration, and the filter cake was washed with deionized water until a pH of 7 was reached. The filter cake was dried for 10 h at 120° C. and calcined at 550° C. for 5 h (heating ramp 2 K/min). A material with a Sn content of 12.3 weight-%, a Si content of 37 weight-%, and a TOC of less than 0.1 weight-% was obtained. The BET specific surface area determined according to DIN 66131 was 400 m$^2$/g, and the crystallinity determined via XRD was 84%.

Reference Example 2

Preparation of a Tin-Containing Zeolitic Material Having BEA Framework Structure and a Sn Content of 9.6 Weight-% Via Incorporation of Tin by Solid-State Ion Exchange (i) Preparation of B-BEA 209 kg de-ionized water were provided in a vessel. Under stirring at 120 rpm (rounds per minute), 355 kg tetraethyl-ammonium hydroxide were added and the suspension was stirred for 10 minutes at room temperature. Thereafter, 61 kg boric acid were suspended in the water and the suspension was stirred for another 30 minutes at room temperature. Subsequently, 555 kg Ludox® AS-40 were added, and the resulting mixture was stirred at 70 rpm for another hour at room temperature. The liquid gel had a pH of 11.8 as determined via measurement with a pH electrode. The finally obtained mixture was transferred to a crystallization vessel and heated to 160° C. within 6 h under a pressure of 7.2 bar and under stirring (140 rpm). Subsequently, the mixture was cooled to room temperature. The mixture was again heated to 160° C. within 6 h and stirred at 140 rpm for additional 55 h. The mixture was cooled to room temperature and subsequently, the mixture was heated for additional 45 h at a temperature of 160° C. under stirring at 140 rpm. 7800 kg de ionized water were added to 380 kg of this suspension. The suspension was stirred at 70 rpm and 100 kg of a 10 weight-% $HNO_3$ aqueous solution was added. From this suspension the boron containing zeolitic material having a BEA framework structure was separated by filtration. The filter cake was then washed with de-ionized water at room temperature until the washing water had a conductivity of less than 150 microSiemens/cm. The thus obtained filter cake was subjected to drying in a nitrogen stream.

The thus obtained zeolitic material was subjected to spray-drying in a spray-tower with the following spray-drying conditions:

| drying gas, nozzle gas: | technical nitrogen |
|---|---|
| temperature drying gas: | |
| temperature spray tower (in): | 235° C. |
| temperature spray tower (out): | 140° C. |
| nozzle: | |
| top-component nozzle | supplier Gerig; size 0 |
| nozzle gas temperature: | room temperature |
| nozzle gas pressure: | 1 bar |
| operation mode: | nitrogen straight |
| apparatus used: | spray tower with one nozzle |
| configuration: | spray tower - filter - scrubber |
| gas flow: | 1,500 kg/h |
| filter material: | Nomex ® needle-felt 20 m$^2$ |
| dosage via flexible tube pump: | SP VF 15 (supplier: Verder) |

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material was then subjected to calcination at 500° C. for 5 h. The calcined material had a $B_2O_3:SiO_2$ molar ratio of 0.045, a total carbon content of (TOC) 0.08 weight-%, a crystallinity determined by XRD of 56%, ad BET specific surface area determined by DIN 66131 of 498 m$^2$/g.

(ii) Deboronation 840 kg de-ionized water were provided in a vessel equipped with a reflux condenser. Under stirring at 40 rpm, 28 kg of the spray-dried and calcined zeolitic material obtained from (i) were employed. Subsequently, the vessel was closed and the reflux condenser put into operation. The stirring rate was increased to 70 rpm. Under stirring at 70 rpm, the content of the vessel was heated to 100° C. within 1 h and kept at this temperature for 20 h. Then, the content of the vessel was cooled to a temperature of less than 50° C. The resulting deboronated zeolitic material having a BEA framework structure was separated from the suspension by filtration under a nitrogen pressure of 2.5 bar and washed four times with deionized water at room temperature. After the filtration, the filter cake was dried in a nitrogen stream for 6 h. The obtained deboronated zeolitic material was subjected to spray-drying under the conditions as described in 5.1. The obtained zeolitic material had a $B_2O_3:SiO_2$ molar ratio of less than 0.002, a water uptake of 15 weight-%, a crystallinity determined by XRD of 48% and a BET specific surface area determined by DIN 66131 of 489 m$^2$/g.

(iii) Incorporation of Sn 25 g of the deboronated zeolitic material having a BEA framework structure obtained from (ii), were added to a mixer (mill type Microton MB550) together with 5.5 g of tin(II) acetate (Sn(OAc)$_2$ [CAS-Nr:638-39-1]), and the mixture was milled for 15 minutes with 14,000 r.p.m. (rounds per minute). After the milling, the mixture was transferred to a porcelain basket and calcined in air at 550° C. for 5 h, with a heating ramp of 2 K/min. The obtained powder material had a Sn content of 9.6 weight-%, a silicon (Si) content of 38 weight-%, and a TOC of less than 0.1 weight-%. The BET specific surface area measured by DIN 66131 was 423 m$^2$/g, the crystallinity determined by XRD 51%, and the water uptake 18 weight-%. The UV/Vis spectrum showed two maxima, one at a wavelength of 200 nm and a second around 250 nm. In the FT-IR spectrum the intensity ratio between a first adsorption band with a maximum between 3701 to 3741 cm$^{-1}$ and a second adsorption with the maximum between 3600 to 3690 cm$^{-1}$ was 1.49.

(iv) Acid Treatment 10 g zeolitic material obtained from (iii) were provided in a round bottom flask and 300 g of a 30 weight-% $HNO_3$ aqueous solution, having a pH in the range of from 0 to 1, were added. The mixture was stirred at a temperature of 100° C. for a period of 20 h (200 r.p.m.). The suspension was filtered and the filter cake was then washed with de-ionized water at room temperature until the washing water had a pH of approximately 7. The obtained zeolitic material was dried at 120° C. for 10 h and calcined by heating to 550° C. (2 K/min) and subsequent heating at 550° C. for 10 h. The dried and calcined zeolitic material had a Si content of 36 weight-%, a Sn content of 9.3 weight-% and a crystallinity determined via XRD of 53%. Further, the zeolitic material had a BET specific surface area, determined according to DIN 66131, of 380 m$^2$/g and a water uptake of 6 weight-%. The UV/Vis spectrum showed two maxima, one at a wavelength of 208 nm and a second around 250 nm. In the FT-IR spectrum the intensity ratio between a first adsorption band with a maximum between 3701 to 3741 cm$^{-1}$ and a second adsorption with the maximum between 3600 to 3690 cm$^{-1}$ was 0.93.

Example 1

Baeyer-Villiger Oxidation of Cyclohexanone to Epsilon-Caprolactone Using a Sn-MWW Having a Sn Content of 0.46 Weight-% and 1,2-Dichloroethane as Solvent with Addition of Potassium Salts General Procedure A 100 ml glass flask vessel was charged with 1.5 g cyclohexanone, 1.2 g zeolitic material obtained according to Reference Example 1.1.1, having a Sn content of 0.46 weight-% and 45 g dichloroethane. The mixture was heated to reflux (95° C.). An aqueous solution of 0.5 g $H_2O_2$ (70 weight-%) was added and the reaction was stirred for 4 h. After cooling down to room temperature, the solution was filtrated and analyzed with respect to the selectivities to epsilon-caprolactone, based on cyclohexanone and based on hydrogen peroxide, by quantitative GC analysis using di-n-butyl ether as internal standard.

Example 1.1

Baeyer-Villiger Oxidation with Addition of Potassium Dihydrogen Phosphate ($KH_2PO_4$) as Potassium Salt

Example 1.1 was carried out according to the General Procedure above, wherein the aqueous solution of hydrogen peroxide additionally contained 360 micromol $KH_2PO_4$ per mol $H_2O_2$. The selectivities to epsilon-caprolactone, based on cyclohexanone and based on hydrogen peroxide, are shown in Table 1 below.

Example 1.2

Baeyer-Villiger Oxidation with Addition of Potassium Dihydrogen Phosphate ($KNO_3$) as Potassium Salt

Example 1.2 was carried out according to the General Procedure above, wherein the aqueous solution of hydrogen peroxide additionally contained 360 micromol $KNO_3$ per mol $H_2O_2$. The selectivities to epsilon-caprolactone, based on cyclohexanone and based on hydrogen peroxide, are shown in Table 1 below.

Example 1.3

Baeyer-Villiger Oxidation with Addition of Potassium Formate ($KCO_2H$) as Potassium Salt

Example 1.3 was carried out according to the General Procedure above, wherein the aqueous solution of hydrogen peroxide additionally contained 360 micromol $KCO_2H$ per mol $H_2O_2$. The selectivities to epsilon-caprolactone, based on cyclohexanone and based on hydrogen peroxide, are shown in Table 1 below.

Comparative Example 1

Baeyer-Villiger Oxidation without Addition of a Potassium Salt

Comparative Example 1.3 was carried out as described in the General Procedure in Example 1 above. The selectivities to epsilon-caprolactone, based on cyclohexanone and based on hydrogen peroxide, are shown in Table 1 below.

Example 2

Continuous-Type Baeyer-Villiger Oxidation of Cyclohexanone to Epsilon-Caprolactone Using a Shaped Sn-MWW Having a Sn Content of 0.46 Weight-% and Acetonitrile as Solvent with Addition of $KH_2PO_4$

General Procedure

A tubular reactor (length: 1.4 m, internal diameter: 7 mm) equipped with a jacket for thermostatization was charged with 15 g of the catalyst obtained according to reference example 1.1.2 above in the form of strands with a diameter of 1.7 mm. The remaining reactor volume was filled with inert material (steatite spheres, 2 mm in diameter, to a height of about 5 cm at the lower end of the reactor and the remainder at the top end of the reactor). The reactor was thermostatized by passing a heat transfer medium, a mixture of water and ethylene glycol, through the jacket. The heat transfer medium was fed at the lower end of the jacket so that it flew in concurrent mode to the reactor contents. The temperature of the heat transfer medium at the entrance of the jacket is defined as the reaction temperature. The flow rate of the heat transfer medium was adjusted on that the difference between entrance and exit temperature was at most 1 K. The pressure in the reactor was controlled by a suitable pressure control valve and maintained constant at 20 bar (abs). The reactor feed stream was metered by using a metering pump. The stream consisted of a mixture of acetonitrile (93.6 weight-%), cyclohexanone (2.5 weight-%), an aqueous hydrogen peroxide solution with a concentration of 40 weight-% (3.9 weight-%) (flow rate: 40 g/h). Under the conditions used the feed was liquid and only one liquid phase was present. The experiment was performed in a continuous manner. At the start of the run (t=0 is defined at which the metering pump was started) the reaction temperature was set to 90° C. After a certain period of time (usually within 4 hours on stream) a stationary state was reached. The reactor effluent after the pressure control valve was collected, weighed and analyzed by GC using di-n-butylether as internal standard.

Specific Procedure

Example 2 was carried out as described in the General Procedure above, wherein the hydrogen peroxide solution used for the preparation of the feed stream additionally contained potassium dihydrogen phosphate in an amount of 360 micromol $KH_2PO_4$ per 1 mol hydrogen peroxide. The selectivities to epsilon-caprolactone, based on cyclohexanone and based on hydrogen peroxide, are shown in Table 1 below.

Comparative Example 2

Baeyer-Villiger Oxidation without Addition of a Potassium Salt

Comparative Example 2 was carried out as described in the General Procedure in Example 2 above. The selectivities to epsilon-caprolactone, based on cyclohexanone and based on hydrogen peroxide, are shown in Table 1 below.

Example 3

Baeyer-Villiger Oxidation of Cyclohexanone to Epsilon-Caprolactone Using a Sn-MWW Having a Sn Content of 12.8 Weight-% and 1,2-Dichloroethane as Solvent with Addition of $KH_2PO_4$

General Procedure

A 100 ml glass flask vessel was charged with 3 g cyclohexanone, 0.1 g zeolitic material obtained according to Reference Example 1.2.1, having a Sn content of 12.8 weight-% and 90 g dichloroethane. The mixture was heated to reflux (95° C.). An aqueous solution of 0.98 g $H_2O_2$ (70 weight-%) was added and the reaction was stirred for 4 h. After cooling down to room temperature, the solution was filtrated and analyzed with respect to the selectivities to epsilon-caprolactone, based on cyclohexanone and based on hydrogen peroxide, by quantitative GC analysis using di-n-butyl ether as internal standard.

Specific Procedure

Example 3 was carried out as described in the General Procedure above, wherein the aqueous solution of hydrogen peroxide additionally contained 360 micromol $KH_2PO_4$ per mol $H_2O_2$. The selectivities to epsilon-caprolactone, based on cyclohexanone and based on hydrogen peroxide, are shown in Table 1 below.

Comparative Example 3

Baeyer-Villiger Oxidation without Addition of a Potassium Salt

Comparative Example 3 was carried out as described in the General Procedure in Example 3 above. The selectivities to epsilon-caprolactone, based on cyclohexanone and based on hydrogen peroxide, are shown in Table 1 below.

Example 4

Baeyer-Villiger Oxidation of Cyclohexanone to Epsilon-Caprolactone Using a Sn-MWW Having a Sn Content of 12.3 Weight-% and 1,2-Dichloroethane as Solvent with Addition of $KCO_2H$ General Procedure A 100 ml glass flask vessel was charged with 1.5 g cyclohexanone, 0.1 g zeolitic material obtained according to Reference Example 1.2.2, having a Sn content of 12.3 weight-% and 45 g 1,2-dichloroethane. The mixture was heated to reflux (95° C.). An aqueous solution of 0.49 g $H_2O_2$ (70 weight-%) was added and the reaction was stirred for 4 h. After cooling down to room temperature, the solution was filtrated and analyzed with respect to the selectivities to epsilon-caprolactone, based on cyclohexanone and based on hydrogen peroxide, by quantitative GC analysis using di-n-butyl ether as internal standard.

Specific Procedure

Example 4 was carried out as described in the General Procedure above, wherein the aqueous solution of hydrogen peroxide additionally contained 360 micromol $KCO_2H$ per mol $H_2O_2$. The selectivities to epsilon-caprolactone, based on cyclohexanone and based on hydrogen peroxide, are shown in Table 1 below.

Comparative Example 4

Baeyer-Villiger Oxidation without Addition of a Potassium Salt

Comparative Example 4 was carried out as described in the General Procedure in Example 4 above. The selectivities to epsilon-caprolactone, based on cyclohexanone and based on hydrogen peroxide, are shown in Table 1 below.

Example 5

Baeyer-Villiger Oxidation of Cyclohexanone to Epsilon-Caprolactone Using a Sn-BEA Having a Sn Content of 9.6 Weight-% and 1,4-Dioxane as Solvent with Addition of $KH_2PO_4$ General Procedure A 100 ml glass flask vessel was charged with 1.5 g cyclohexanone, 1 g zeolitic material obtained according to Reference Example 2, having a Sn content of 9.6 weight-% and 45 g 1,4-dioxane. The mixture was heated to reflux (95° C.). An aqueous solution of 0.5 g $H_2O_2$ (70 weight-%) was added and the reaction was stirred for 4 h. After cooling down to room temperature, the solution was filtrated and analyzed with respect to the selectivities to epsilon-caprolactone, based on cyclohexanone and based on hydrogen peroxide, by quantitative GC analysis using di-n-butyl ether as internal standard.

Specific Procedure

Example 5 was carried out as described in the General Procedure above, wherein the aqueous solution of hydrogen peroxide additionally contained 360 micromol $KH_2PO_4$ per mol $H_2O_2$. The selectivities to epsilon-caprolactone, based on cyclohexanone and based on hydrogen peroxide, are shown in Table 1 below.

Comparative Example 5

Baeyer-Villiger Oxidation without Addition of a Potassium Salt

Comparative Example 5 was carried out as described in the General Procedure in Example 5 above. The selectivities to epsilon-caprolactone, based on cyclohexanone and based on hydrogen peroxide, are shown in Table 1 below.

TABLE 1

Results of the Examples and Comparative Examples

| Example (E) Comparative Example (CE) | Sn zeolite catalyst | | | | Selectivities[4] to product[2] based on | |
|---|---|---|---|---|---|---|
| | framework structure type | Sn incorporation via | Sn content/ weight-% | Potassium additive | hydrogen peroxide/% | starting material[3] |
| E1.1 | MWW | HS | 0.46 | $KH_2PO_4$ | 59 | 66 |
| E1.2 | | | | $KNO_3$ | 52 | 58 |
| E1.3 | | | | $KCO_2H$ | 59 | 69 |
| CE1 | | | | — | 51 | 54 |
| E2 | MWW | HS | 0.46 | $KH_2PO_4$ | 13 | 50 |
| CE2 | | | | — | 12 | 40 |
| E3 | MWW | SSIE | 12.8 | $KH_2PO_4$ | 13 | 18 |
| CE3 | | | | — | 10 | 15 |

TABLE 1-continued

Results of the Examples and Comparative Examples

| Example (E) Comparative Example (CE) | Sn zeolite catalyst | | | | Selectivities[4] to product[2] based on | |
|---|---|---|---|---|---|---|
| | framework structure type | Sn incorporation via | Sn content/ weight-% | Potassium additive | hydrogen peroxide/% | starting material[3] |
| E4 | MWW | SSIE | 12.3 | KCO$_2$H | 32 | 37 |
| CE4 | | | | — | 26 | 33 |
| E5 | BEA | SSIE | 9.6 | KH$_2$PO$_4$ | 95 | 82 |
| CE5 | | | | — | 80 | 76 |

[1] HS = hydrothermal synthesis; SSIE = solid-state ion exchange
[2] epsilon-caprolactone
[3] cyclohexanone
[4] The selectivities were calculated based on the concentrations of the starting material and the product in the product mixture determined by quantitative GC analysis using di-n-butylether, and the known amount of H$_2$O$_2$ and starting material at the beginning of the reaction The examples and the comparative examples clearly show that irrespective of the zeolitic framework structure type, irrespective of the tin content of the zeolitic material, and irrespective of the chemical nature of the potassium salts employed, the addition of a potassium salt to the oxidation reaction and, thus, the catalytic system of the tin containing zeolitic material and the potassium salt, leads to improved selectivities to the product, based on the starting material to be oxidized as well as based on hydrogen peroxide. Therefore, since it is these selectivities which have the most important impact on whether or not a process is interesting for industrial purposes, the process and the catalytic system according to the invention are especially suitable for medium and large scale processes. This is also illustrated by example E2 and comparative example CE2 which represent a continuous-type process where the catalyst consists of strands comprising the tin-containing zeolitic material and the catalytic system of the zeolitic material and the potassium salt additive is realized as fixed-bed catalytic system which is of particular relevance in industrial scale processes. Still further, it is shown that the improved characteristics are obtained irrespective of how the tin-containing zeolitic material is prepared since the advantageous selectivity values are obtained for zeolitic materials prepared by solid-state tin-ion exchange as well as by the incorporation of tin via hydrothermal synthesis. Yet further, it is also shown the advantageous selectivity values are obtained irrespective of the solvent employed since in the examples and comparative examples above, different solvents were used, and for each solvent, the advantageous effects were obtained.

Summarized it is shown that the inventive process and the inventive catalytic system represent an overarching conceptual framework realized by the combination of a potassium salt additive and a tin-containing zeolitic material used in Baeyer-Villiger-type oxidation reactions.

CITED LITERATURE

Nature 412 (2001), pages 423-425
Journal of Catalysis 234 (2005), pages 96-100
U.S. Pat. No. 5,968,473
U.S. Pat. No. 6,306,364
Microporous and Mesoporous Materials 165 (2013), pages 210-218
WO 03/074422 A1
U.S. Pat. No. 7,326,401 B2
M. A. Camblor, A. Corma, M.-J. Diaz-Cabanas and Ch. Baerlocher, J. Phys. Chem. B 102 (1998) pages 44-51

The invention claimed is:

1. A catalytic system comprising a catalyst comprising a tin-containing zeolitic material having a BEA structure and at least one potassium salt, wherein the at least one potassium salt is selected from the group consisting of at least one inorganic potassium salt, at least one organic potassium salt, and combinations of at least one inorganic potassium salt and at least one organic potassium salt wherein
   the at least one inorganic potassium salt is selected from the group consisting of potassium hydroxide, potassium halides, potassium nitrate, potassium sulfate, potassium hydrogen sulfate, potassium hydrogen phosphate, potassium dihydrogen phosphate, and potassium perchlorate,
   the at least one organic potassium salt is selected from the group consisting of potassium carbonate, potassium hydrogen carbonate, potassium salts of aliphatic saturated carboxylic acids having from 1 to 6 carbon atoms tricarboxylic acids having from 4 to 10 carbon atoms or tetracarboxylic acids,
   and
   wherein the tin-containing zeolitic material has a tin content in the range from 0.2 to 20 weight-%, based on the total weight of the tin-containing zeolitic material.

2. The catalytic system of claim 1, wherein the tin-containing zeolitic material has a tin content in the range of from 0.1 to 25 weight-% based on the total weight of the tin-containing zeolitic material.

3. The catalytic system of claim 1, wherein the tin-containing zeolitic material has a tin content in the range of from 0.4 to 15 weight-%, based on the total weight of the tin-containing zeolitic material.

4. The catalytic system of claim 1, wherein at least 95 weight of the zeolitic framework structure consist of SiO$_2$, B$_2$O$_3$ and Sn.

5. The catalytic system of claim 4, wherein at least 99.9 weight-% of the zeolitic framework structure consist of SiO$_2$, B$_2$O$_3$ and Sn.

6. The catalytic system of claim 1, wherein the catalyst is the tin-containing zeolitic material in the form of a powder or spray-powder, or is a molding comprising the tin-containing zeolitic material, wherein the tin-containing zeolitic material is comprised in the molding, and if a powder then at least 90 weight-% of the powder or spray-powder consist of the tin-containing zeolitic material.

7. The catalytic system of claim 1, wherein the catalyst is the tin-containing zeolitic material in the form of a powder or spray-powder, wherein at least 99.9 weight-% of the powder or spray-powder consist of the tin-containing zeolitic material.

8. A process for the oxidation of an organic carbonyl compound of formula (I)

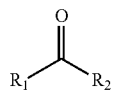
(I)

wherein $R_1$ and $R_2$ are independently from one another a linear or branched alkyl residue, a linear or branched alkenyl residue, an aryl or heteroaryl residue, or a hydrogen atom with the proviso that $R_1$ and $R_2$ are not simultaneously a hydrogen atom, said process comprising (i) providing a liquid mixture comprising the compound of formula (I), hydrogen peroxide, at least one at least partially dissolved potassium salt, and optionally a solvent;

(ii) reacting the compound of formula (I) with the hydrogen peroxide in the liquid mixture in the presence of the catalyst comprising tin containing zeolite material wherein the catalyst and the potassium salt form the catalytic system according to claim 1, to provide a compound of formula (II)

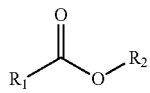
(II)

wherein, if neither $R_1$ nor $R_2$ is a hydrogen atom, $R_1$ and $R_2$ may form, together with the carbonyl group or the carboxyl group, a ring and the compound of formula (I) is

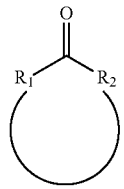

and the compound of formula (II) is

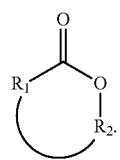

9. The catalytic system of claim 1, wherein at least 98% by weight of the zeolitic framework structure consist of $SiO_2$, $B_2O_3$ and Sn.

10. The catalytic system of claim 1, wherein the catalytic system is obtained by contacting the zeolitic material with a liquid feed stream comprising said potassium salt.

11. The catalytic system of claim 1, wherein at least 99% by weight of the zeolitic framework structure consist of $SiO_2$, $B_2O_3$ and Sn.

12. The catalytic system of claim 1, wherein at least 99.5% by weight of the zeolitic framework structure consist of $SiO_2$, $B_2O_3$ and Sn.

13. The catalytic system of claim 1, wherein at least 99.8% by weight of the zeolitic framework structure consist of $SiO_2$, $B_2O_3$ and Sn.

* * * * *